(12) United States Patent  
Malish

(10) Patent No.: US 11,786,747 B2
(45) Date of Patent: Oct. 17, 2023

(54) TREATMENT USING INDIVIDUALIZED TRANSCRANIAL MAGNETIC STIMULATION

(71) Applicant: WellBrain LLC, Canyon Lake, TX (US)

(72) Inventor: Shannon Lea Malish, Spring Branch, TX (US)

(73) Assignee: WellBrain LLC, Canyon Lakes, TX (US)

( * ) Notice: Subject to any disclaimer, the term of this patent is extended or adjusted under 35 U.S.C. 154(b) by 0 days.

(21) Appl. No.: 17/811,053

(22) Filed: Jul. 6, 2022

(65) Prior Publication Data

US 2022/0355125 A1 Nov. 10, 2022

Related U.S. Application Data

(63) Continuation-in-part of application No. 17/143,716, filed on Jan. 7, 2021.

(51) Int. Cl.
*A61N 2/00* (2006.01)

(52) U.S. Cl.
CPC .................. *A61N 2/006* (2013.01)

(58) Field of Classification Search
CPC .................. A61N 2/006; A61N 2/02
See application file for complete search history.

(56) References Cited

U.S. PATENT DOCUMENTS

| 6,066,163 A | 5/2000 | John |
| 8,926,490 B2 | 1/2015 | Phillips et al. |
| 9,015,057 B2 | 4/2015 | Phillips et al. |
| 10,029,111 B2 | 7/2018 | Jin |
| 10,420,482 B2 | 9/2019 | Jin |
| 10,420,953 B2 | 9/2019 | Jin |

(Continued)

FOREIGN PATENT DOCUMENTS

WO 2013172981 A1 11/2013

OTHER PUBLICATIONS

P.G. Janicak et al., "Transcranial magnetic stimulation for the treatment of major depression," Neuropsychiatr. Dis Treat., vol. 11, pp. 1549-1560, Jun. 26, 2015.

(Continued)

*Primary Examiner* — Christine H Matthews
(74) *Attorney, Agent, or Firm* — FOX ROTHSCHILD LLP

(57) ABSTRACT

Systems and methods for treatment of a mental disorder of a subject are disclosed. The methods include receiving a first set of electroencephalography ("EEG") measurements that each correspond to brain activity at one or more of a plurality of zones of a brain of the subject. The methods further include determining a target frequency for the subject based on the first set of EEG measurement where, the target frequency being an EEG frequency where the brain of the subject operates optimally across a plurality of EEG channels in an alpha brainwave, and generating a treatment protocol for the subject based on the target frequency. The treatment protocol includes one or more individualized transcranial magnetic stimulation (TMS) treatments that each include application a plurality of magnetic stimulation pulses for a defined time period and at a frequency of about the target frequency.

20 Claims, 11 Drawing Sheets

(56) References Cited

U.S. PATENT DOCUMENTS

| | | |
|---|---|---|
| 11,311,741 B2 | 4/2022 | Phillips et al. |
| 2011/0130615 A1 | 6/2011 | Mishelevich |
| 2014/0058189 A1* | 2/2014 | Stubbeman ............ G16H 20/10 600/13 |

OTHER PUBLICATIONS

P.G. Janicak et al., "The Efficacy of Transcranial Magnetic Stimulation for Major Depression: A Review of the Evidence," Psychiatric Annals, vol. 44, No. 6, nn. 284-292, Jun. 24, 2014.
"Transcranial magnetic stimulation," Wikipedia, 17 pages, retrieved from https://en.wikipedia.org/w/index.php?title=Transcranial_magnetic_stimulation&oldid=971762254, last edited Aug. 8, 2020.

* cited by examiner

TREATMENT USING INDIVIDUALIZED TRANSCRANIAL MAGNETIC STIMULATION

CROSS-REFERENCE AND CLAIM OF PRIORITY

This patent application is a continuation-in-part of and claims priority to U.S. patent application Ser. No. 17/143,716 filed Jan. 7, 2021, which is incorporated herein in its entirety.

TECHNICAL FIELD

This invention relates to individualized transcranial magnetic stimulation, and more particularly to diagnosing and treatment of particular disease states in neurology and mental health.

BACKGROUND

Mental disorders can present as painful, debilitating, and very costly for the affected individual and their family. The lack of treatment often leads to debilitating and life threatening consequences. The standard method of diagnosing mental disorders has been with either the Diagnostic and Statistical Manual of Mental Disorders 5th edition ("DSM5") or the International Statistical Classification of Diseases and Related Health Problems ("ICD"). Both standards primarily involve diagnosis through a mental health provider's personal interview with the subject regarding symptoms and behaviors. As such, both the interviewer and the subject may introduce their own subjective bias into the process. Furthermore, the subject may not accurately report due to perceived negative implications.

As a result, there is a desire for better techniques of diagnosing and treating mental disorders, including alcohol and substance abuse disorders, based on measurable objective data.

SUMMARY

Systems and methods for treatment of a mental disorder of a subject are disclosed. In one or more scenarios, the methods may include, by a processor: receiving a first set of electroencephalography ("EEG") measurements where the first set of EEG measurements correspond to brain activity at one or more of a plurality of zones of a brain of the subject. Next, a target frequency for the subject may be determined based on the first set of EEG measurements that is an EEG frequency where the brain of the subject operates optimally across a plurality of EEG channels in an alpha brainwave. The methods may also include generating a treatment protocol for the subject based on the target frequency, and causing a TMS system to provide the one or more treatments to the subject in accordance with the treatment protocol. The treatment protocol may include one or more individualized transcranial magnetic stimulation (TMS) treatments that each include application a plurality of magnetic stimulation pulses for a defined time period and at a frequency of about the target frequency. Optionally, a treatment interval maybe interspersed between two consecutive TMS treatments.

Optionally, the TMS treatments may include applying magnetic stimulation pulses to a Cz zone, a Fz zone, an F3 zone, and an FPZ zone of the brain of the subject, wherein the Cz, Fz, F3, and FPZ zones correspond to those zones as designated within a 10-20 system of electrode placement.

In various implementations, determining the target frequency can include averaging PSD values across a plurality of EEG channels and aligning the average with a nearest Heart Rate Frequency.

In certain implementations, the methods can also include receiving a second set of EEG measurements after the causing the TMS system to provide the one or more treatments to the subject in accordance with the treatment protocol, updating the target frequency to generate an updated target frequency based on the second set of EEG measurements, and generating a second treatment protocol based on the updated target frequency. Optionally, an intertrain interval of the treatment protocol may be different than an intertrain interval of the second treatment protocol.

In one or more implementations the target frequency can be about 8-12 Hz.

Optionally, the target frequency can be updated to align with a heart rate frequency of the subject.

In various implementations, the methods may also include receiving a second set of EEG measurements after the causing the TMS system to provide the one or more treatments to the subject in accordance with the treatment protocol, and displaying an improvement in the mental disorder as a movement of a greatest frequency associated with one or more of a plurality of EEG channel closer to the target frequency. Optionally, a change in the mental disorder that is less than a threshold may be determined based on a comparison of the first set of EEG measurement and the second set of EEG measurements, and the treatment protocol may be updated to include a first TMS treatment that comprises application of about 200 to 400 magnetic stimulation pulses at about 30% amplitude to the F3 zone of the brain of the subject.

In various implementation, the mental disorder can include, for example, traumatic brain injury; tinnitus; short term memory issues; substance abuse disorder; sleep disorder; anxiety; depression; post-traumatic stress disorder; attention deficit hyperactivity disorder; bi-polar disorder; dementia; sleep disorders; balance and fine motor skills disorder; reading comprehension; verbal communication, and working memory disorders; night vision disorders; or colors and shape vision disorders.

Implementing systems of the above-described methods for image classification and can include, but are not limited to, a processor and a non-transitory computer-readable storage medium comprising programming instructions that are configured to cause the processor to implement the above methods. Optionally, the programming instructions may be included in a computer program product.

DETAILED DESCRIPTION

Figure 1:
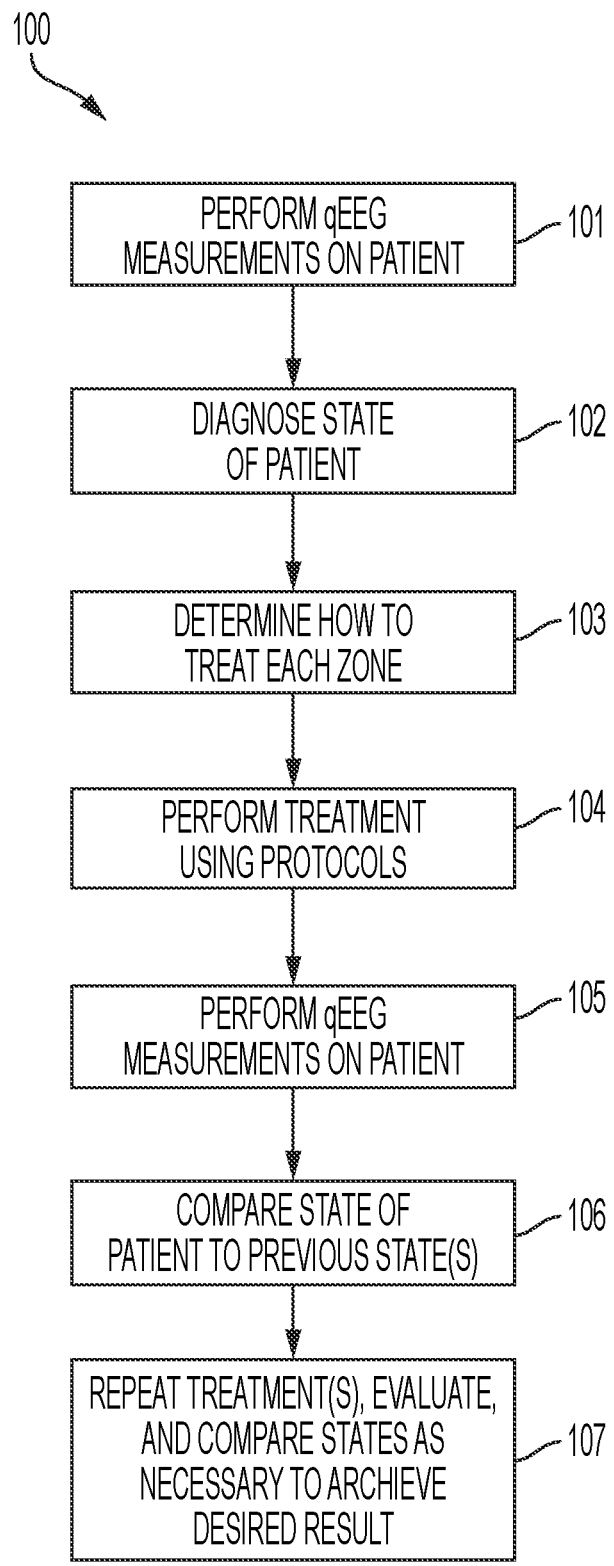
FIG. 1 illustrates a flowchart diagram configured in accordance with embodiments of the present disclosure.

The brain is an integrated command center that has 86 million neurons. When these neurons are out of sync, the condition is referred to as brain arrhythmia, which has been proven to be the cause for many brain-related diseases and abnormal conditions. Embodiments of the present disclosure diagnose any brain arrhythmia within a subject's brain and provide treatment to bring the frequencies in all areas of the brain back in balance to promote mental wellness. By analyzing EEG scans and optional psychometric assessments, embodiments of the present disclosure create an individualized plan for Transcranial Magnetic Stimulation to align neurons in different parts of the brain to work synchronously in the same frequency.

The following definitions will be used in describing embodiments of the present disclosure:

As used in this specification and the appended claims, the singular forms "a," "an," and "the" include plural references unless the context clearly dictates otherwise. Thus, for example, references to "a subject" includes one or more subjects described herein which will become apparent to those persons skilled in the art upon reading this disclosure and so forth. Any reference to "or" herein is intended to encompass "and/or" unless otherwise stated.

As used in this specification and the appended claims, the term "about" means that the stated parameter can vary by as much as 0.1%, as much as 1%, as much as 5%, as much as 10%, as much as 20%, as much as 50% in various embodiments.

It is understood that where a parameter range is provided, all integers within that range, and tenths thereof, are also provided by the invention. For example, "0.1-2.5" includes 0.1, 0.2, 0.3, etc. up to 2.5.

"Treating" (or treat) as used herein encompasses, e.g., inducing inhibition, regression, or stasis of a disease or disorder, or lessening, suppressing, inhibiting, reducing the severity of, eliminating or substantially eliminating, or ameliorating a symptom of the disease or disorder.

As used herein, "subject" or "individual" (used interchangeably) means a mammal, preferably a human mammal. The term "subject" does not require the oversight (either continuous or intermittent) of a medical or scientific professional (e.g., a physician, nurse, physician's assistant, clinical research associate, orderly, and hospice worker); however, the term does not preclude the oversight of a medical or scientific professional.

Transcranial Magnetic Stimulation ("TMS"): A noninvasive form of brain stimulation by applying a changing magnetic field to cause electric current at a specific area of the brain through electromagnetic induction used to treat Depression, Migraine, and OCD.

Quantitative electroencephalography ("qEEG"): An analysis of digitized EEG measurements taken on a subject during an EEG examination. In lay terms, this is also referred to as "Brain Mapping" (three-dimensional).

Channel: An EEG electrode capturing brainwave activity (i.e., EEG measurements).

Zone: Different selected regions of the brain for which brainwave activity is measured. Such zones may be selected to correspond to the EEG electrode channels utilized in the 10-20 system, which is an internationally recognized method to describe and apply the location of scalp electrodes in the context of an EEG examination/scan.

Homeostatic Frequency: The Homeostatic Frequency is the Alpha wave frequency associated with Alpha brainwaves at which a brain operates as measured by the qEEG at the time of the EEG measurement. Specifically, the Homeostatic Frequency is the Alpha wave frequency where the brain operates optimally in maximum of the EEG channels as measured by the qEEG (i.e., when most of the brain neurons are aligned to fire at the same time). This frequency may vary at different zones of the brain. Optionally, the Homeostatic Frequenc(ies) for a subject at a given time may be determined from a qEEG Report as the frequency at which the peaks (i.e., Greatest Frequencies) across multiple EEG channels are approximately aligned (as discussed below with respect to FIGS. 9A and 9B).

Alpha brainwaves are dominant during quietly flowing thoughts, and in some meditative states. Alpha is the resting state for the brain. Alpha brainwaves aid overall mental coordination, calmness, alertness, mind/body integration, and learning.

The optimal Homeostatic Frequency of a normal healthy brain should lie between about 8-12 Hz. However, the measured Homeostatic Frequency of a brain may shift because of certain brain disorders (e.g., depression, anxiety, sleep disorders, ADHD, etc.), trauma (emotional and/or physical) to the brain, substance abuse, or the like. For purposes in accordance with certain embodiments of the present disclosure, an "optimal Homeostatic" Alpha wave frequency for a particular subject is also referred to herein as the "Target Frequency." Specifically, a Target Frequency is an Alpha wave frequency at which a subject's brain should be operating optimally in maximum of the EEG channels when functioning normally. A Target Frequency may be about 7 Hz-13 Hz, about 8-12 Hz, about 9-11 Hz, or the like. Optionally, the Target Frequency for a subject may be determined by taking the average PSD values across all EEG channels and aligning this average with the nearest Heart Rate Frequency (as discussed below with respect to FIGS. 9A and 9B).

Greatest Frequency: The frequency, for each channel, at which most of the neurons fire during the period of conducting an EEG examination. This is the frequency with the maximum PSD (as defined herein) for each channel.

Pulse: A single magnetic stimulation with a TMS system.

Train: The period (seconds) of magnetic stimulation required for the Pulse Rate.

Pulse Rate: The number of Pulses in a Train.

InterTrain: The period (seconds) of pause between Trains.

Amplitude: The power setting prescribed for magnetic stimulation. The higher the Amplitude, the stronger the stimulation.

Power Spectrum/Spectral Density ("PSD"): A Power Spectral Density is the measure of a signal's power (voltage) content versus frequency. A PSD is typically used to characterize broadband random signals. The amplitude of the PSD may be normalized by the spectral resolution employed to digitize the signal.

The power spectrum $S_{xx}(f)$ of a time series x(t) describes the distribution of power into frequency components composing that signal. According to Fourier analysis, any physical signal can be decomposed into a number of discrete frequencies, or a spectrum of frequencies over a continuous range. The statistical average of a certain signal or sort of signal (including noise) as analyzed in terms of its frequency content, is called its spectrum.

When ale energy of the signal is concentrated around a finite time intergyral, especially if its total energy is finite, one may compute the energy spectral density. More commonly used is the power spectral density (or simply, power spectrum), which applies to signals existing over all time, or over a time period large enough (especially in relation to the duration of a measurement) that it could as well have been over an infinite time interval. The PSD then refers to the spectral energy distribution that would be found per unit e, since the total energy of such a signal over all time would generally be infinite. Summation or integration of the spectral components yields the total power (for a physical process) or variance (in a statistical process), identical to what would be obtained by integrating $x^2(t)$ over the time domain, as dictated by Parseval's theorem. See MarcAntoine Parseval des Chênes, "Mémoire sur les séries et sur l'intégration complète d'une équation aux différences partielles linéaire du second ordre, á coefficients constants," presented before the Académie des Sciences (Paris) on Apr. 5, 1799. This article was published in "Mémoires présentés á l'Institut des Sciences, Lettres et Arts, par divers savants, et lus dans ses assemblées. Sciences, mathématiques et physiques. (Savants &rangers)," vol. 1, pp. 638-648 (1806), which is hereby incorporated by reference herein.

During the course of conducting an EEG examination, at each channel the PSD for a frequency is a measure of how many times brainwaves of that frequency were observed. It can be thought of as relative power or dominance of that frequency.

To compute the homeostatic brain-wave frequency, the average power of a signal in a specific frequency range (e.g., 2-20 Hz) is calculated, which includes computing a single number that summarizes the contribution of the given frequency to the overall power of the signal. This implies the decomposition of the EEG measurement signal into frequency components, which is achieved through a Fast Fourier Transform. Then the magnitude-squared of the FFT is taken to obtain an estimate of the PSD.

Embodiments of the present disclosure utilize the Welch Method to compute the PSD, which includes averaging consecutive Fourier transform of small windows of the signal, with or without overlapping. See P. D. Welch, "The Use of Fast Fourier Transform for the Estimation of Power Spectra: A Method Based on Time Averaging Over Short, Modified Periodograms," IEEE Transactions on Audio and Electroacoustics, Vol. AU-15, No. 2, June, 1967, which is hereby incorporated by reference herein.

The EEG measurement signal can be represented as sequence of data values or samples:
x[0], x[1], . . . , x[N−1]

The data sequence ranges from 0 to N−1. The data values x[n] are indexed by their sample number n. This is the sample value's position relative to the start of the sequence.

The data samples are acquired at a constant rate. The time between two successive data samples x[n] and x[n+1] is T seconds. The sample rate is 1/T' samples per second. The length of the data sequence in seconds is $T_{seq}=N*T$. The time of acquisition of a data value is related to its sample number by $t=t_0+nT$ where $t_0$ is time when the first data sample was acquired.

The procedure to calculate PSD can be mathematically described by the following steps:

1. EEG data sequence:
x[0], x[1], . . . , x[N−1]
Is partitioned into K segments or batches:
Segment 1: x[0], x[1], . . . , x[M−1]
Segment 2: x[S], x[S+1], . . . , x [M+S−1]
:
Segment K: x [N−M], x [N−M+1], . . . , x [N−1]
where,
M=Number of points in each segment or batch
S=Number of points to shift between segments
K=Number of segments or batches 2. For each segment (k=1 to K), compute a windowed Discrete Fourier Transform ("DFT") at some frequency v=i/M with $$-\left(\frac{M}{2}-1\right) \le i \le \frac{M}{2}:$$

$$X_k(v) = \sum_m x[m]w[m]e^{-j2\pi vm}$$

where, m=(k−1) S, . . . , M+(k−1) S−1, and
w [m]=the window function (taper function).

3. For each segment (k=1 to K), form the modified periodogram value, $P_k(f)$, from the discrete Fourier transform:

$$P_k(v) = \frac{1}{W}|X_k(v)|^2$$

Where, $$W = \sum_{m=0}^{M} w^2[m]$$

4. Average the periodogram to obtain estimate of PSD:

$$S_x(v) = \frac{1}{K}\sum_{k=1}^{K} P_k(v)$$

Welch's method is also called the Weighted Overlapped Segment Averaging ("WOSA") method and periodogram averaging method. The parameter M is the length of each segment. Note that M is the length of the DFT. The parameter S is the number of points to shift between segments. It is the number of new points in each segment or batch.

The number of points in common to two adjacent segments is M−S. Two adjacent segments are said to overlap by M−S points or 100[(M−S)/M]%.

A FFT is a fast algorithm for computing the DFT in Step 2 of the above method. The M-point sequence w[m] is the window function. Some common windows are the rectangular, Hann, Hamming, Blackman, Blackman-Harris, and Kaiser-Bessel.

The squaring and averaging may be performed in the frequency domain in Steps 3 and 4. Step 3 forms the periodogram or sample spectrum.

The units for $P_k$ (V) are the same as those for $S_x$ (v), i.e., $V^2/Hz$. The $P_k$ (V) may not be good estimates of PSDs because they may contain too much statistical oscillation. Step 4 averages the periodograms $P_k$ (V) to form a stable PSD estimate that does not oscillate wildly.

In accordance with embodiments of the present disclosure, exemplary parameters utilized for the above steps may be:

In Step 1, take 256 points at a time (M=256), and shift the window by 128 points (S=128). Thus, two adjacent segments overlap by 50%. The shift between segments S is usually in the range 0.4M<S<M.

In Step 2, take Hann as the window function, since it yields improved sensitivity specificity and reduced spectral leakage.

In accordance with embodiments of the present disclosure, the unit of PSD is converted from $V^2/Hz$ to $\mu V^2/Hz$.

Embodiments of the present disclosure provide predictive diagnostics for mental health diagnosing by providing systems and methods for utilizing qEEG measurements of an individual to diagnose or assist in the diagnosis of a neurological or mental disease state for that individual. Embodiments of the present disclosure further provide systems and methods for generating an individualized transcranial magnetic stimulation ("iTMS") protocol (including one or more TMS sessions at determined individualized frequencies) for the individual to achieve a Target Frequency as the Homeostatic Frequency in order to treat the diagnosed state, and administering the generated iTMS protocol. Optionally, the iTMS protocol may be updated based on collected EEG readings after one or more iTMS sessions during the iTMS protocol in order to determine updated Target Frequency for the individual.

Embodiments of the present disclosure are applicable to the diagnosis and treatment of all neurological or mental disease states (for the sake of simplicity, these will be simply referred to herein as "mental states"), including, but not limited to, Major Depressive Disorder ("MDD"), addictions of various types, anxiety, sleep disorders, substance abuse, traumatic brain injury/concussion, Attention Deficit Hyperactivity Disorder ("ADHD"), issues associated with menopause, executive functions, early onset Dementia, eating disorders, tinnitus, anger problems, short-term memory loss, Obsessive-Compulsive Disorder ("OCD"), migraines, improvement of athletic performance, balance problems, and other brain disorders. Embodiments of the present disclosure may be utilized for in subject and out subject centers or by a therapeutic practitioner specializing in addiction, anxiety, depression, Bipolar Disorder, ADHD, sleep disorders, chronic pain, and other mental health and neurological disorders.

As described herein, embodiments of the present disclosure provide systems and methods to diagnose and/or treat the emotional and psychological health of a subject through the use of iTMS, which balances deficits in the brain, whether caused by organic damage, physical damage, or emotional/trauma damage. Embodiments of the present disclosure "repair" these areas of the brain with customized protocols unique to each individual subject's brain based upon one or more qEEG measurements made during the diagnosis and/or during treatment.

Referring to FIG. 1, there is illustrated systems and methods 100 configured in accordance with embodiments of the present disclosure. In the process block 101, qEEG measurements are performed on a subject in a manner as further described herein. In the process block 102, the results of the qEEG measurements are used solely or in combination with other evaluation techniques to diagnose the subject for one or more mental states. In the process block 103, the diagnosis determined in the process block 102 will be used to determine how to treat selected zones using an iTMS system. In the process block 104, the iTMS system is utilized to perform the treatments determined in the process block 103 in accordance with one or more predetermined protocols. At some designated time after the performed treatments, another set of qEEG measurements are performed on the subject to determine how such qEEG measurements have changed due to the treatment performed in the process block 104. In accordance with certain embodiments of the present disclosure, one or more additional evaluation techniques may be performed to assess the progress of the mental state(s) of the subject. In the process block 106, the current mental presentation of the subject is compared to one or more previously determined mental states in order to evaluate and analyze how the previous treatment(s) have affected the diagnosed mental state(s) of the subject. The process block 107 represents that any one or more of the process blocks 101-106 may be repeated in order to achieve a desired result (e.g., change) in the mental state(s) of the subject.

Figure 6:
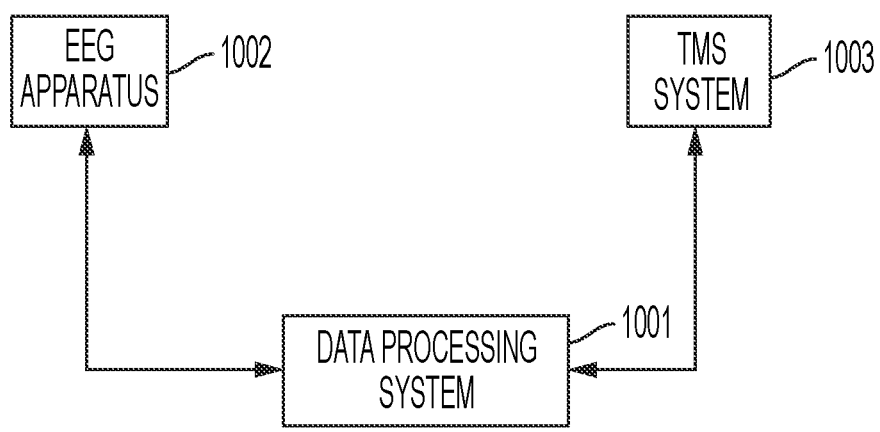
FIG. 6 illustrates a block diagram configured in accordance with embodiments of the present disclosure.

The EEG examinations/scans performed in the systems and methods 100 may be performed utilizing any well-known apparatus suitable for doing so (e.g., see the EEG apparatus 1002 of FIG. 6 described herein). For example, individually placed electrodes or a cap having pre-positioned electrodes may be applied to the subject's head in accordance with the 10-20 system.

Figure 2:
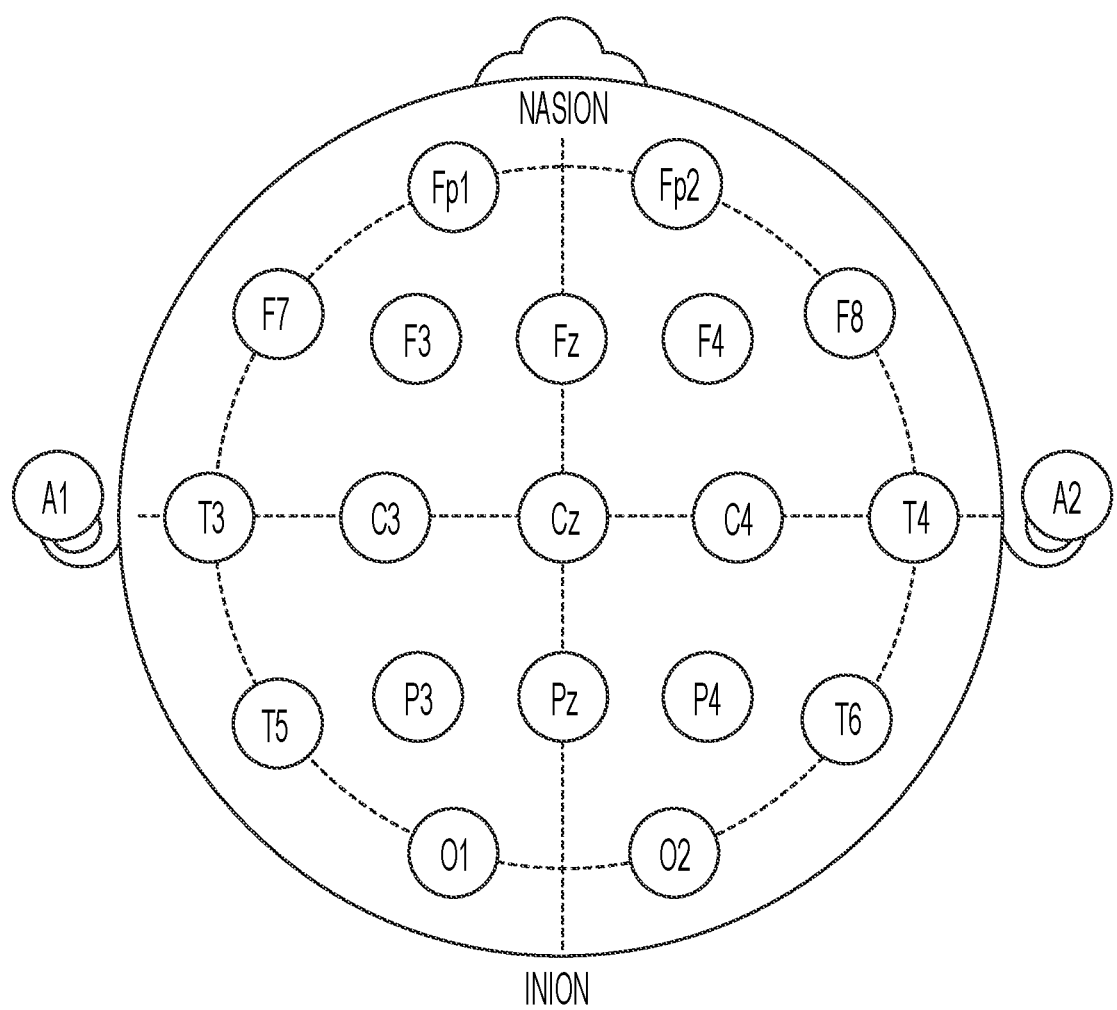
FIG. 2 illustrates EEG electrodes/channels according to the 10-20 system of electrode placement.

Referring to FIG. 2, there is illustrated the electrode labeling for such a 10-20 system. It has been determined that the electrodes can be utilized to analyze the following common functions in a subject, but are not limited to:

Fp1—Situational awareness, judgement, vigilance, irritability, depression, foggy headedness, disorganization, analytical area Fp2—Impulsivity (restraint of impulses), decision control, perseveration, social awareness, manic and panic behavior, emotional inhibition, avoidance behaviors, tactlessness Fz—Execution functions, linear tasks, working memory, absent mindedness, personality changes, intention and motivation F3—Verbal impulse control, motor planning, short-term memory, planning and problem solving, facial recognition, deducting facts to conclusions F4—Judgement and planning, motor planning ("makes the plan"), short-term memory, spatial-object memory, inductive creative, attentional area F7—Language, reading comprehension, verbal expression, working memory (visual and auditory), word retrieval, semantics, divided and selective attention F8—Emotional availability, emotional expression (anger, joy, happiness), sustained attention, conscious facial emotional processing Cz—Primary somatosensory, gross motor function C3—Right-sided somatosensory; fine motor skills, i.e., hand and digits (with F3, handwriting), feeling of pain, pressure, warmth C4—Left-sided somatosensory; fine motor skills, feeling of pain, pressure, warmth T3—Verbal memory and reading comprehension, long-term memory (verbal and visual), "inner voice" positive mood, auditory processing, sound perception, thyroid T4—Emotional memory, auditory processing, sound perception, anger, sadness, thyroid Pz—Visual memory, cognitive processing, dreaming, self-awareness P3—Cognitive Processing (verbal reasoning), depth perception, excessive thinking, integration of self-imagination, spelling, math calculations, complex grammar (right side of body awareness)

P4—Visuospatial memory, analytical skills, self-concern, map orientation, music, body image, knowing difference between right and left, (left side body awareness)

P7—Secondary visual processing, night vision

P8—Secondary visual processing, color, shapes

O1—Primary visual processing, visual acuity

O2—Primary visual processing, visual acuity, depth perception

A1, A2—Ear Clip Reference Points for heart rate

Note that not all areas and functions of the brain are ubiquitous for all subjects.

In accordance with embodiments of the present disclosure, these mapped functions may be utilized to diagnose a mental state of a subject, and to depict the progress made with respect to a subject as they proceed through treatment protocols as described herein.

Figure 3A:
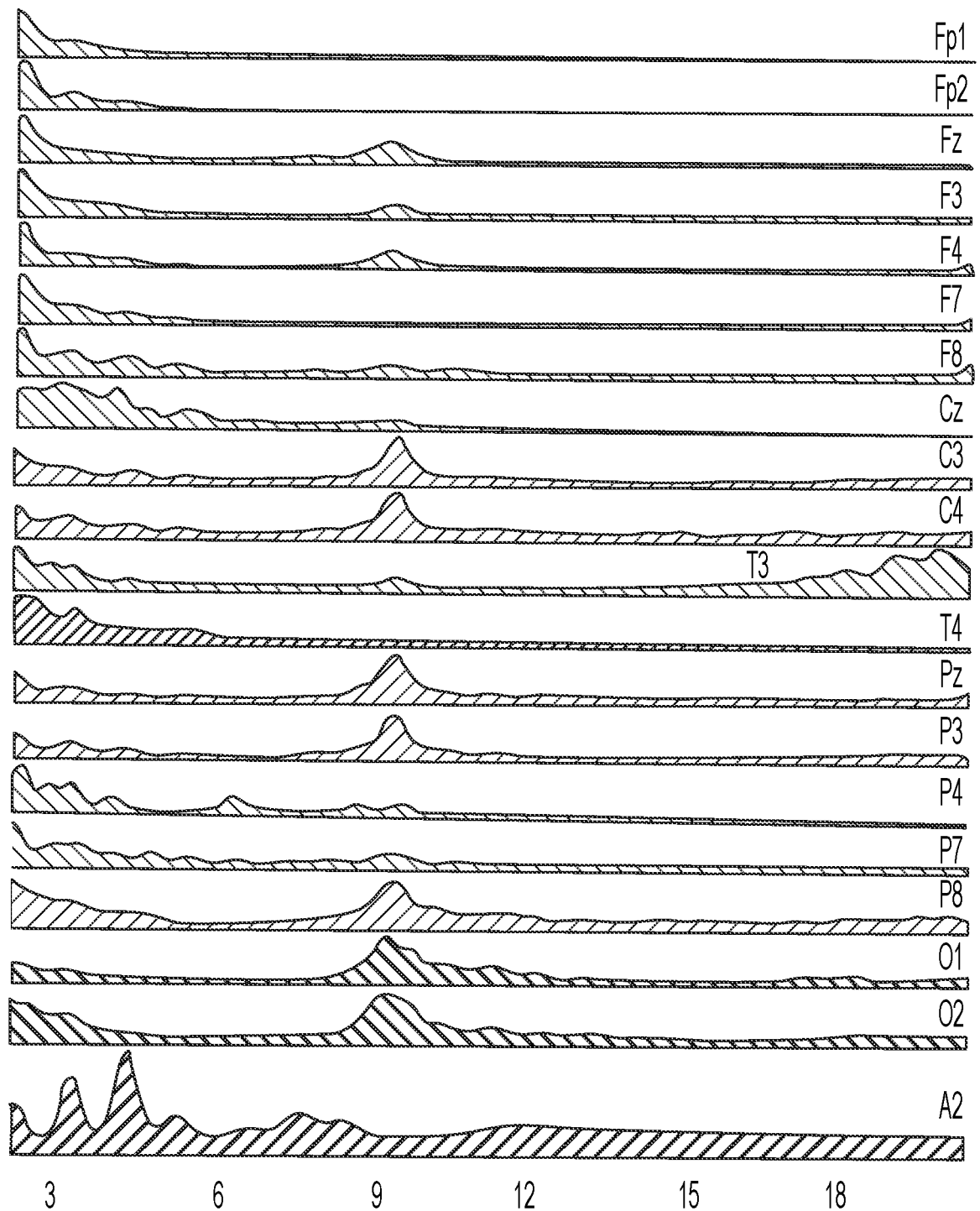
FIGS. 3A-3B illustrate a non-limiting example of qEEG Reports produced from EEG measurements taken on a sample subject. For each area of the brain (e.g., the locations corresponding to the EEG electrodes), a graph is produced. The x-axis represents the frequencies of brain activity. The y-axis represents the power/voltage of the measured signal. Each point on the graph represents the power generated at a specific frequency.

FIG. 3A illustrates a non-limiting example of a qEEG Report in which EEG measurements were taken on a sample subject, such as would be performed in the process block 101. Each of the PSD plots in the qEEG Report depicts the recorded PSD values on the y-axis and measured brain-wave frequencies (Hz) on the x-axis corresponding to each 10 of the EEG electrodes. During the course of the qEEG measurements, the PSD of a frequency is a measure of how many times brainwaves of that frequency were observed.

As described herein, a healthy brain should exhibit a single Homeostatic Frequency (i.e., the maximum PSD) across all regions of the brain. In other words, the Greatest Frequency for each channel should be in the range of 8-12 Hz (i.e., within the alpha wave region), and should be substantially the same (i.e., substantially aligned) for all channels. This means that all neurons in the brain should be synchronously firing with substantially the same frequency falling within the alpha wave region. Though this is true for some of the channels in the exemplary qEEG Report in FIG. 3A, not all of the channels exhibit the Greatest Frequency within the alpha wave region.

Figure 3B:
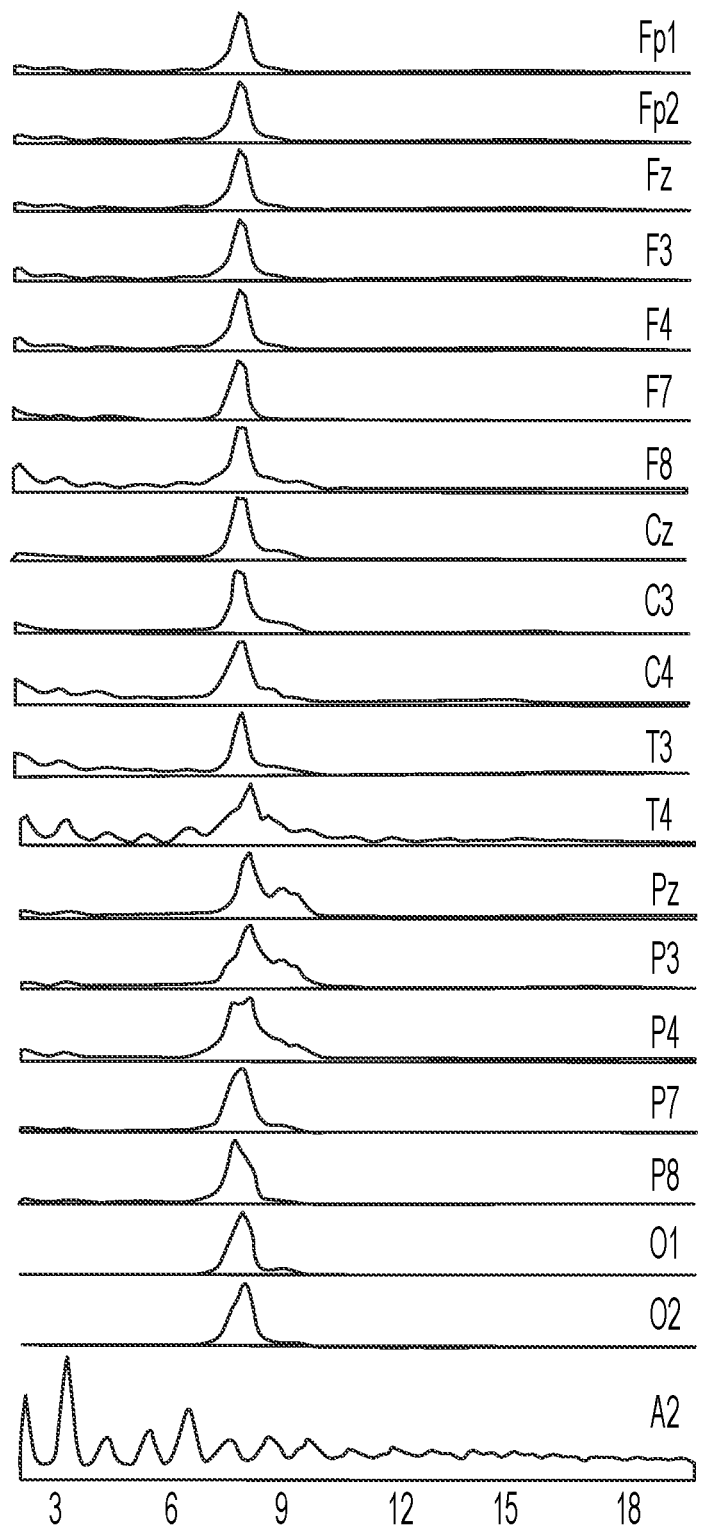

As noted elsewhere herein, brain arrhythmia has been proven to be a cause for many brain-related diseases and abnormal conditions. The Greatest Frequency is the frequency in which most neurons are firing at that portion of the brain (i.e., pertaining to the channel corresponding to that portion of the brain). Therefore, in order to make the substantially entire brain function at the same frequency, the Greatest Frequencies for each channel should be aligned toward the same frequency, which is referred to herein as the Target Frequency. In other words, the measured Homeostatic Frequency is moved towards the Target Frequency. Embodiments of the present disclosure utilize individualized transcranial magnetic stimulation from a TMS system (see FIG. 7) to align the Greatest Frequencies of each channel to the Target Frequency. Specifically, the Homeostatic Frequenc(ies) in a qEEG are moved towards the Target Frequency using the iTMS systems and methods of this disclosure. This is illustrated in FIG. 3B in which one or more treatments in accordance with embodiments of the present disclosure have been performed on the subject to eventually align the Greatest Frequencies for all of the channels. Additionally and/or alternatively, the Target Frequency may be updated as treatment sessions stimulate brain activity and the average PSD values shift.

A qEEG Report may be annotated so that each of the PSD plots has a corresponding indicator, such as color, to indicate in relative terms how close the Greatest Frequency of the brainwaves for a particular channel are to a desired frequency, i.e., the Target Frequency. If the Greatest Frequency of the brainwaves for a particular channel is substantially near (e.g., within a predetermined threshold difference) the Target Frequency, the PSD plot for that channel may be shown in a particular color (e.g., purple). A nonlimiting exemplary color-coding scheme that may be used to display the PSD plots in a qEEG Report is summarized in Table 1.

TABLE 1

| COLOR | DIFFERENCE BETWEEN GREATEST FREQUENCY AND TARGET FREQUENCY (Hz) |
| --- | --- |
| Purple | Less than 0.1 |
| Blue | Between 0.1 and 2.5 |
| Green | Between 2.5 and 5 |
| Yellow | Between 5 and 7.5 |
| Red | 7.5 or Greater |

The color coding in the qEEG Report may be based on the difference between Greatest Frequency and Target Frequency for each channel. The color coding captures how aligned the Greatest Frequency is with the desired Target Frequency, and may thus enhance the qEEG Report to the treating physician and the subject. Persons of ordinary skill in the art will recognize that any other suitable visualization scheme may be utilized instead of color, such as shades of grey, shading patterns, labels, etc.

Figure 4:
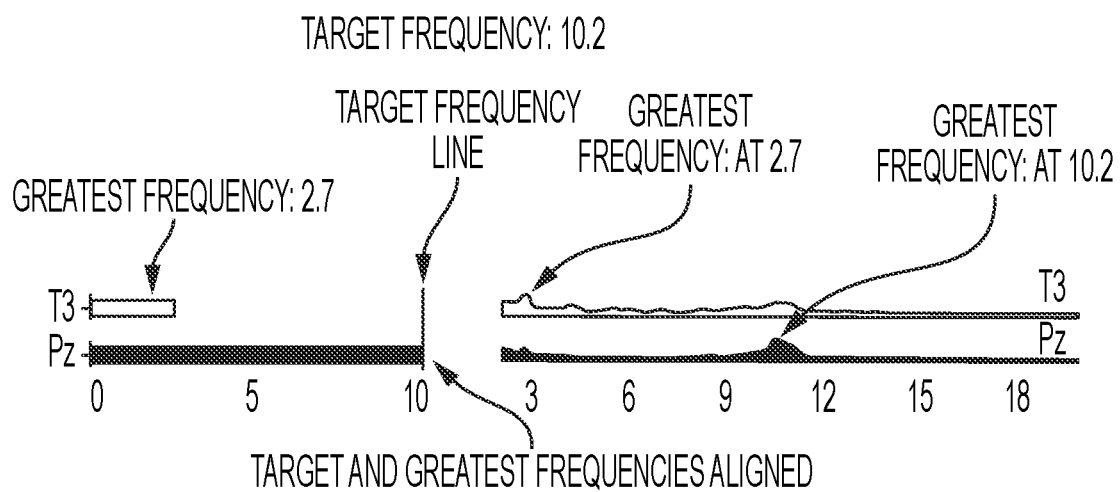
FIG. 4 represents a non-limiting example of a comparison of a sample subject's Greatest Frequency to a Target Frequency for a couple of channels.

The example illustrated in FIG. 4 explains an exemplary color-coding scheme. In this non-limiting example, it has been determined that the Target Frequency for this subject is 10.2 Hz. As can be seen, the subject's PSD plot for the T3 channel is recorded to have a Greatest Frequency of 2.7 Hz. Therefore, it can be determined that there is an irregular brainwave in this portion of the subject's brain. The current Greatest Frequency for the Pz channel is recorded to be 10.2 Hz, which coincides with the Target Frequency line. It can be determined that this portion of the subject's brain is functioning well. The difference between the Greatest Frequency and the Target Frequency for the T3 channel is 7.5 Hz, and 0 Hz for the Pz channel. As a result, the is displayed or printed out qEEG Report for the subject may have a red color for representing the T3 channel and a purple color for representing the Pz channel.

A qEEG Report such as the example illustrated in FIG. 3A may be generated for each qEEG performed on the subject. As demonstrated with respect to the example of FIG. 4, each qEEG Report may be utilized to identify "brain arrhythmia" (i.e., irregular brainwave frequencies that are not aligned with the determined Target Frequency of the subject). In accordance with embodiments of the present disclosure, for different zones of the brain (e.g., channels as recorded by electrodes identified in the 10-20 system), the recorded Greatest Frequency is compared with the Target Frequency, which has been determined to be the frequency in which the subject's brain should be functioning. In addition to the qEEG Report, the recorded Greatest Frequencies pertaining to each channel may be output (e.g., displayed and/or printed) by bar plots. FIG. 4 illustrates only a couple of such bar plots (i.e., pertaining to the channels T3 and Pz), but a bar plot may be produced for each of the channels.

In those cases where all neurons in the brain are firing synchronously with the same frequency falling in the Alpha brainwave region, the recorded Greatest Frequency for each of the channels should coincide with the Target Frequency line. In FIG. 4, the Greatest Frequency is substantially aligned with the Target Frequency for the channel Pz. FIG. 3B illustrates where the Greatest Frequencies of all of the channels are substantially aligned.

If there is irregular brainwave frequency for some portion of the subject's brain, then the Greatest Frequency bar will not coincide with the Target Frequency line, which is depicted for the channel T3. As described with respect to FIG. 4, the bars may be colored based on how close the Greatest Frequency is to the Target Frequency, as per Table 1, though any other distinguishing aspect may be used (e.g., different grey shades, patterns, etc.).

Essentially, embodiments of the present disclosure infuse the subject's homeostatic energy into each area of the brain that is out of sync with the subject's Hoemostatic Frequency, thus creating neuro-modulation so all neurons fire harmoniously. If a subject's brain rhythm in Alpha state is unbalanced, then this unbalance can lead to one or more mental disorders as described herein. As previously noted, embodiments of the present disclosure utilize transcranial magnetic stimulation from a TMS system to align the Greatest Frequencies of each channel to the Target Frequency in order to essentially "balance" the brain rhythm (e.g., see FIG. 3B).

Figure 5:
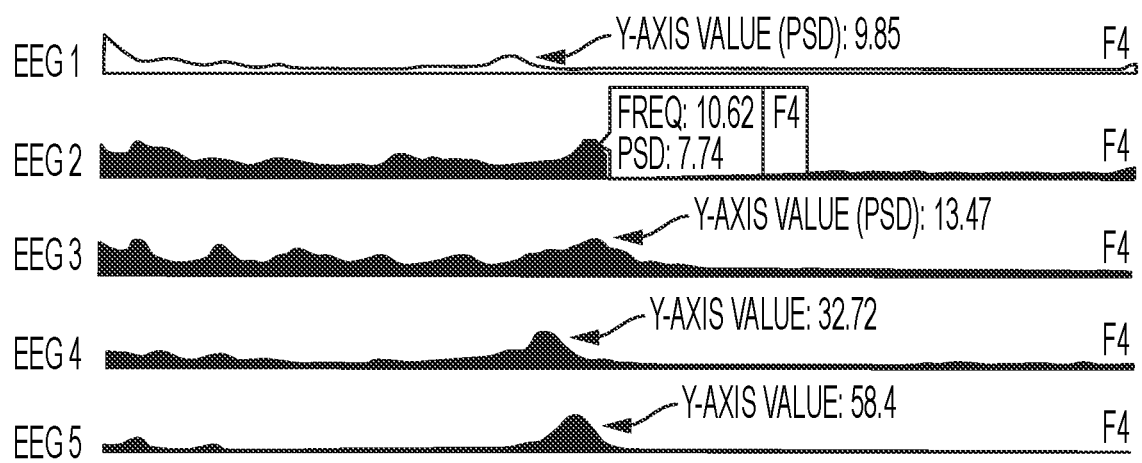
FIG. 5 illustrates a non-limiting example of an Overall Progress Grouped Chart depicting comparisons of a greatest Power Spectral Density ("PSD") value for a particular channel corresponding to EEG measurements of a sample subject over a series of different dates.

Referring to FIG. 5, an Overall Progress Grouped Chart can be output to show the greatest value of y-axis (PSD) of frequency in a range 7 Hz-13 Hz for a particular channel, which can be used to compare and contrast with qEEG measurements of different dates. For example, suppose five EEG examinations were taken for a subject over a period of time (depicted in FIG. 5 as EEG 1, EEG 2, EEG 3, EEG 4, and EEG 5), and considering only one channel for simplicity, in this case the F4 channel, the Overall Progress Grouped Chart depicts how the Greatest Frequency (corresponding to the maximum PSD) for the channel F4 moved over time.

As described with respect to FIG. 1, after one or more initial qEEG measurements have been made on a subject (see the process block 101), a mental state of the subject is diagnosed in the process block 102.

Diagnosing a subject according to conventional techniques and methodologies requires time and proper information. Often times this information is skewed. The subject providing the answers to the clinician may be mentally ill or drug dependent, and therefore may be effectively "challenged" to accurately answer a question, or at times may be a poor historian due to the illness.

Embodiments of the present disclosure overcome such issues by providing an objective assessment of the subject through an analysis of the qEEG measurements, which indicates which areas of the subject's brain are negatively impacted by their particular mental state. In accordance with certain embodiments, traditional psychometric assessments may also be given to the subject. Then, the results of such psychometric assessments may be compared with the objective assessment.

As previously described with respect to FIGS. 3A-4, the objective assessment involves recording qEEG measurements of the subject's brain activity, which can then be represented as a bar graph. For example, if the bar graph shows that the Greatest Frequencies for the Fp1, Fp2, Fz, F3, and F4 channels are below a baseline balance, then the subject may be diagnosed with ADHD. If desired, the practitioner can confirm this diagnosis with one or more traditional psychometric assessments, which may be administered prior to the qEEG and recorded by the software. The bar graph may be compared to the subject's answers. This may also be confirmed using the DSM-5. Such a more informed diagnosis allows psychiatrists to medicate correctly and licensed clinicians to deploy the proper therapeutic intervention, which can save months of diagnostic gathering, which could result in a wrong diagnosis. Furthermore, embodiments of the present disclosure provide practitioners an objective view of the brain movement over time enabling them to determine if the subject answered the subjective psychometric assessments incorrectly.

Applicant has determined that there are distinctive qEEG Reports that correlate to particular mental states. This was confirmed after conducting hundreds of qEEG measurements on numerous different subjects. In other words, characteristics of particular mental states correspond to certain identifiable recorded PSD measurements within a qEEG Report, and thus, embodiments of the present disclosure are capable of diagnosing with significant accuracy a mental state of a subject as a function of the qEEG Report produced by conducting qEEG measurements on the subject. For example, the following mental states or disorders can be diagnosed in a subject based on these characteristics of the qEEG Report:

Anxiety:

Persons with anxiety disorders frequently have intense, excessive and persistent worry and fear about everyday situations. Often, anxiety disorders involve repeated episodes of sudden feelings of intense anxiety and fear or terror that reach a peak within minutes (panic attacks). These feelings of anxiety and panic interfere with daily activities, are difficult to control, are out of proportion to the actual danger, and can last a long time. Such persons may avoid places or situations to prevent these feelings. Symptoms may start during childhood or the teen years and continue into adulthood.

Indication: An individual may be diagnosed with anxiety disorder if the graph on the right side of the Greatest PSD for one or more channels has a "thickness" that is greater than a threshold, as determined below.

"Thickness" is determined for each of the EEG channels by averaging the PSD values in a range of about 13 Hz to about 20 Hz, about 14-19 Hz, about 15-18 Hz, about 16-17 Hz, or the like, to the right of the Greatest Frequency, wherein the average PSD is calculated as a percentage of the recorded PSD at the Greatest Frequency for each of the FP1 through O2 channels. (For example, if the Greatest Frequency is recorded to be 9 Hz at channel F4, the mean of the recorded PSD values from about 13-20 Hz, would be converted into a percentage of the recorded PSD at the Greatest Frequency at channel F4).

The calculated PSD percentages for channels FP1 through O2 are then averaged. If this average (or "thickness") is greater than or equal to about 10-25%, about 12-23%, about 14-21%, about 16-19%, about 15%, about 14%, about 16%, or the like for a subject, then Anxiety is indicated (e.g., diagnosed) for this subject.

Depression:

Depression is a mood disorder that causes a persistent feeling of sadness and loss of interest. Also called major depressive disorder or clinical depression, it affects how one feels, thinks, and behaves, and can lead to a variety of emotional and physical problems. Many have trouble performing normal day-to-day activities, and sometimes may feel as if life is not worth living.

Indication: An individual may be diagnosed with depression disorder if PSDs for one or more channels (e.g., the Fp1, Fp2, Fz, F3, F4, F7, F8, Cz, C3, C4, T3, T4, and Pz channels) on left side of the Greatest Frequency has a "thickness" that is greater than a threshold, as determined below.

"Thickness" is determined for each of the above depression related channels by averaging the PSD values in a range of about 2-8 Hz, about 3-7 Hz, about 4-6 Hz, or the like to the left of the Greatest Frequency, wherein the average PSD is calculated as a percentage of the recorded PSD at the Greatest Frequency for each of the FP1 through O2 channels. (For example, if the Greatest Frequency is recorded to be about 9 Hz at channel F4, the mean of the recorded PSD values from about 2 Hz to 8 Hz would be converted into a percentage of the recorded PSD at the Greatest Frequency at channel F4.)

The calculated PSD percentages for channels FP1 through O2 are then averaged. If this average (i.e., "thickness") is greater than or equal to about 10-25%, about 12-23%, about 14-21%, about 16-19%, about 15%, about 14%, about 16%, or the like for a subject, then Depression is indicated (e.g., diagnosed) for this subject.

Post-Traumatic Stress Disorder ("PTSD"):

Indication: PSD values from about 7 Hz to about 13 Hz frequency spectrum at particular channels, wherein below 50% of the highest PSD from about 3-7 Hz or about 13-20 Hz is determined as described below.

This is indicated at channels F8 and T4. The mean of the recorded PSD values is calculated across entire frequency spectrum for each of channels F8 and T4. The mean for each channel is then converted to a percentage using the average of the PSD values at the Greatest Frequencies for all other channels. These PSD values calculated at channels F8 and T4 are then averaged together. If this average is less than or equal to about 25-60%, about 30-55%, about 35-50%, about 40-45%, or the like of the mean Greatest Power percentage for all other channels, then PTSD is indicated (e.g., diagnosed).

Attention Deficit Hyperactivity Disorder ("ADHD"):

Indication: An individual may be diagnosed with ADHD if the average of the PSD value at target frequency of about 7-13 Hz, about 8-12 Hz, about 9-11 Hz, or the like, in channels Fp1, Fp2, Fz, F3, F4, and F7 is less than about 10-25%, about 12-23%, about 14-21%, about 16-19%, about 15%, about 14%, about 16%, of the average of the highest PSD value for those same channels from about 3-7 Hz, about 4-6 Hz, about, 13 to 20 Hz, about 14-19 Hz, about 15-18 Hz, about 16-17 Hz, or the like.

ADHD is indicated at channels Fp1, Fp2, Fz, F3, F4, and F7. The mean of the recorded PSD values is calculated across entire frequency spectrum for each of channels Fp1, Fp2, Fz, F3, F4, and F7. The mean for each is then converted to a percentage using the average of the PSD values at the Greatest Frequencies for all other channels.

These PSD percentages calculated at channels Fp1, Fp2, Fz, F3, F4, and F7 are then averaged together. If this average is less than or equal to about 10-25%, about 12-23%, about 14-21%, about 16-19%, about 15%, about 14%, about 16%, or the like of the mean Greatest Frequency percentage for all other channels, then ADHD is indicated (e.g., diagnosed).

Bi-Polar Disorder:

Indication: Bi-polar is a mood disorder. An individual may be diagnosed with a bipolar disorder if there are two distinct and individual PSD elevations (peaks) at or within about 6-13 Hz, about 7-12 Hz, about 8-11 Hz, about 9-10 Hz, or the like, at one or more of the channels listed below.

(This may be invalid if the subject is currently taking mood stabilizing medications and or drugs (e.g., Benadryl or alcohol.)

Bipolar disorder may be indicated (e.g., diagnosed) at 5 or more of the following channels (Fp1, Fp2, Fz, F3, F4, F7, F8, Cz, C3, C4, T3, T4, Pz, P3, P4, P7, P8, O1, and O2 channels).

Dementia:

Indication: An individual may be diagnosed with a dementia disorder Greatest Frequency (of one or more channels) is determined to be below about 7-8 Hz.

Specifically, dementia may be indicated if the mean frequency across all channels is determined to be less than about 7-8 Hz. This means that in a relaxed Alpha state, the subject demonstrates PSD values at a frequency lower than about 7-8 Hz. This usually happens when a person is asleep.

Concussion/Traumatic Brain Injury ("TBI"):

An individual may be diagnosed with a TBI disorder if the high-pointed spikes of approximately the same PSD at about 6-7 Hz or less are observed across five or more channels (e.g., Fp1, Fp2, Fz, F3, F4, F7, F8, Cz, C3, C4, T3, T4, Pz, P3, P4, P7, P8, O1, and O2 channels). A high-pointed spike may be represented by narrow (e.g., width less than about 0.2-0.4 Hz, about 0.2 Hz, about 0.3 Hz, about 0.4 Hz, or the like) elevated PSD values. Such groups of "spikes," also called clusters, occur when the natural homeostatic rhythm is disrupted by concussion or TBI, or a brain injury is so severe that the brain pattern in five or more channels has shifted and does not return to its natural homeostatic rhythm. The spikes can be in any five of the 19 channels/zones of the brain (location depending on where the brain was impacted). In some example, if these spikes align with the heart rate spikes, then this indication may be ruled out.

Balance & Fine Motor Skills (Cz, C3, and C4):

Balance and coordination problems are any problems that are uncharacteristic of that person's normal state. For example, stumbling, clumsiness, dizziness when standing, etc. are all indications of this problem.

Indication: An individual may be diagnosed with balance and coordination problems if the PSD value at target frequency from about 7-13 Hz, about 8-12 Hz, about 9-11 Hz, or the like, in channel Cz is less than about 10-25%, about 12-23%, about 14-21%, about 16-19%, about 15%, about 14%, about 16%, or the like of the highest PSD value from about 3 and 7 Hz or from about 13 and 20 Hz.

Fine Motor Skills on the right side refer to issues with hand and fingers, pressure or pain on right side. Indication: PSD value at target frequency from about 7-13 Hz, about 8-12 Hz, about 9-11 Hz, or the like, in channel C3 is less than about 10-25%, about 12-23%, about 14-21%, about 16-19%, about 15%, about 14%, about 16%, or the like, of the highest PSD value from about 3 and 7 Hz or from about 13 and 20 Hz.

Fine Motor Skills on the left side refer to issues with hand and fingers, pressure or pain on right side. Indication: PSD value at target frequency from about 7-13 Hz, about 8-12 Hz, about 9-11 Hz, or the like, in channel C4 is less than about 10-25%, about 12-23%, about 14-21%, about 16-19%, about 15%, about 14%, about 16%, or the like, of the highest PSD value from about 3 and 7 Hz or from about 13 and 20 Hz.

Reading comprehension, verbal communication, and working memory F7:

Indication: PSD value at target frequency from about 7-13 Hz, about 8-12 Hz, about 9-11 Hz, or the like, in channel F7 is less than is less than about 10-25%, about 12-23%, about 14-21%, about 16-19%, about 15%, about 14%, about 16%, or the like, of the highest PSD value from about 3 and 7 Hz or from about 13 and 20 Hz.

Night vision P7:

Indication: PSD value at target frequency between from about 7-13 Hz, about 8-12 Hz, about 9-11 HZ, or the like, in channel P7 is less than about 10-25%, about 12-23%, about 14-21%, about 16-19%, about 15%, about 14%, about 16%, or the like of the highest PSD value from about 3 and 7 Hz or from about 13 and 20 Hz.

Colors, Shapes:

Indication 1: PSD value at target frequency from about 7-13 Hz, about 8-12 Hz, about 9-11 HZ, or the like, in channel P8 is less than about 10-25%, about 12-23%, about 14-21%, about 16-19%, about 15%, about 14%, about 16%, or the like of the highest PSD value from about 3 and 7 Hz or from about 13 and 20 Hz.

Indication 2: PSD value at target frequency from about 7-13 Hz, about 8-12 Hz, about 9-11 HZ, or the like, in channels O1 and O2 is less than about 10-25%, about 12-23%, about 14-21%, about 16-19%, about 15%, about 14%, about 16%, or the like of the highest PSD value from about 3 and 7 Hz or from about 13 and 20 Hz.

Embodiments of the present disclosure are not limited to the foregoing mental states, and may also include tinnitus, short term memory issues, substance abuse disorder, sleep disorder, and a combination of depression and anxiety.

Referring to FIG. 10, in accordance with embodiments of the present disclosure, PSD characteristics particular to one or more mental states may be programmed into algorithms run in one or more software programs performed within a data processing system 1001. The EEG apparatus 1002, which may be used to make the EEG measurements, may be coupled (e.g., by a network connection) to the data processing system 1001 so that a qEEG Report can be produced by the data processing system 1001 so that the various PSD measurements can be analyzed by the algorithms to output a diagnosis of a mental state for a subject in accordance with the process block 102 of FIG. 1. Such algorithms may be programmed using any well-known programming language, including one that implements a machine learning system, as will be described in further detail herein. Alternatively, the EEG measurements may be entered into the data processing system 1001 as data files produced by the EEG apparatus 1002. Such data files may be in a "Brain Vision" format that includes the raw EEG data, a header file, and a marker file. The header file may include information about the number of channels, the number of data points, and the sampling interval used. The data files may include the raw EEG data in an IEEE Float32 format. The marker file may include information about the file name of the raw data file and the encoding used such as UTF-8. A Python library called "MNE" may be used to read the data files.

Before describing how embodiments of the present disclosure utilize iTMS to treat a subject for mental state(s) diagnosed in the process block 102, a TMS system 1003 will be described.

Transcranial magnetic stimulation ("TMS") is a noninvasive form of brain stimulation in which a changing magnetic field is used to cause electric current at a specific area of the brain through electromagnetic induction. An electric pulse generator, or stimulator, is connected to a magnetic coil, which in turn is connected to the scalp. The stimulator generates a changing electric current within the coil which induces a magnetic field; this field then causes a second inductance of inverted electric charge within the brain itself. Based on the principle of electromagnetic induction, TMS modulates the brain's electrical environment using magnetic fields, which pass through the scalp and skull unimpeded. These fields are produced by passing rapidly alternating electrical currents through a coil with a ferromagnetic core (i.e., an electromagnet in lieu of a permanent magnet). The magnetic field strength produced by TMS may vary from 1.5 to 3 teslas (T), and is comparable to an MRI device, except that it focuses on a limited area of the cortex using a circular, figure-eight, conical, or helmet-like coil design (e.g., H-coil). TMS can be administered in single pulses or as a brief series of pulses, called a train, for research, diagnostic, and therapeutic purposes. When used clinically, several thousand pulses may be applied over a period of minutes to hours. This is referred to as repetitive transcranial magnetic stimulation or "rTMS." These pulses can be delivered in a rapid (i.e., >1-20 Hz) repetitive fashion, enhancing cortical activity; or in a slow (i.e., <1 Hz) repetitive fashion, inhibiting cortical activity.

Figure 7:
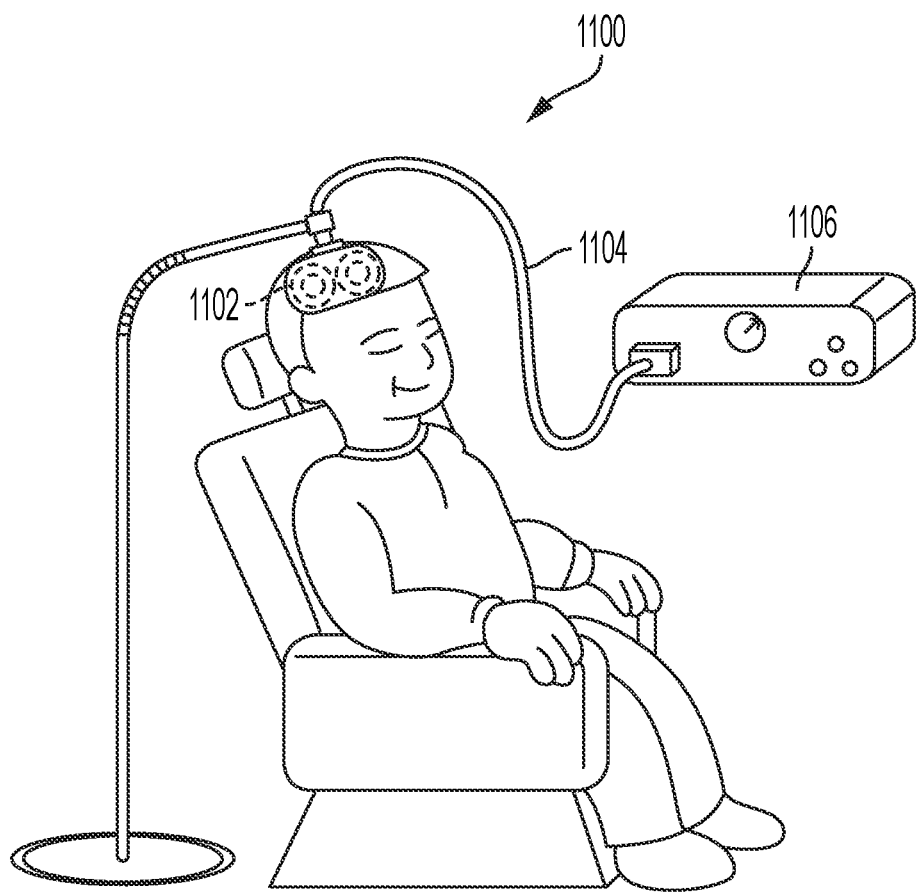
FIG. 7 illustrates a schematic diagram of a TMS system.

As shown in FIG. 7, a typical TMS system 1100 includes a stimulation coil (magnetic field generation means) 1102 and a magnetic stimulation control unit 1106 electrically connected to the stimulation coil 1102 through a cable 1104. The TMS system 1100 is designed to treat and/or ease certain symptoms by applying magnetic stimulation with certain intensity into the cranial nerve of the subject by means of the stimulation coil 1102 positioned in proximity to the scalp of the subject.

The stimulation coil 1102 is designed so that it can generate a variable magnetic field, which applies the magnetic stimulation onto at least specific positions of the subject (i.e., in proximity to selected zone of the subject's brain). Various types of conventional magnetic coils are available for the stimulation coil 1102. For example, the stimulation coil 1102 may be configured as a so-called figure eight-shape coil having a configuration made by placing two spiral coils on the same plane in the form of a number eight. This allows that an application of electric current to this figure eight-shaped coil in the same direction as shown in the drawing, for example, generates the maximum inductive current density immediately beneath the overlapped portions of the spirals.

The magnetic stimulation control unit 1106, which is designed to control an application of electric current pulses to the stimulation coil 1102, may use any one of several conventional units. The magnetic stimulation control unit 1106 may be manually operated by an operator. In the operation, the operator can control various settings such as magnitude and/or waveform of the current pulses determining the intensity of magnetic stimulation and/or the stimulation cycle or interval stimulation (e.g., the Pulse Rate, Train, and InterTrain) with a TMS system. The software produces a custom protocol of the Pulse Rate, Train and Intertrain.

Referring again to FIG. 1, embodiments of the present disclosure utilize the mental state diagnosis of the subject determined in the process block 102 to determine a treatment plan for treating certain selected zone(s) (process block 103). In accordance with embodiments of the present disclosure, to begin the objective assessment for a diagnosis of a subject's mental state, the Target Frequency is determined. A set of qEEG measurements may be used to determine the Target Frequency. In accordance with embodiments of the present disclosure, the Target Frequency is the maximum recorded frequency at which the subject's brain effectively operates (determined using the methods described below), and will be used to establish the Target Frequency for other zones (e.g., EEG channels of the brain). As described herein, a goal is to improve frequency alignment across all brain zones. In other words, to achieve the "Homeostatic Frequency" for that subject's brain throughout all or at least desired zones.

The initial EEG measurements are converted into a representational graph (i.e., the PSD report) that shows where the subject's brain is balanced and where deficits exist, such as described herein with respect to FIGS. 3A-5. This may be followed by a face-to-face consult with the subject, and determination of the optimal "target" wave frequency (i.e., the Target Frequency to achieve for each of the zones) and how the "target" can change with time. Embodiments of the present disclosure are able to capture this information and then create a treatment plan (process block 103). After the Target Frequency is ascertained, in the process block 104, the subject undergoes iTMS treatment with the TMS system 1003, which may be performed using one or more various standard iTMS protocols, such as described herein.

Referring to the Brain Map diagram of FIG. 2, as previously noted, these are particular regions (zones) of the brain in which EEG channels may be utilized to measure brainwave activity. There are numerous brainwaves, measured in hertz (Hz), constituted on an EEG to include Delta, Theta, Alpha, Beta, and Gamma waves, which transition from low to high frequency, respectively. Embodiments of the present disclosure utilize iTMS to specifically target Alpha brainwaves. Often people with depression, anxiety, substance use, ADHD, OCD, and so forth commonly have elevated brainwaves outside the Alpha range and often have a suppression with the Alpha brainwaves. Elevation and suppression of brainwaves relates to the amplitude, represented on the y-axis where frequency remains on the x-axis. In accordance with embodiments of the present disclosure, each subject's Homeostatic Frequency is observed from the brainstem to the prefrontal cortex, and used to determine a Target Frequency to be achieved using the iTMS treatment protocols. This allows a tailored approach created by the software in the data processing system 1001 to stimulate this unique frequency and increase amplitude with the utilization of magnetic stimulation from the TMS system 1003.

Figure 9A:
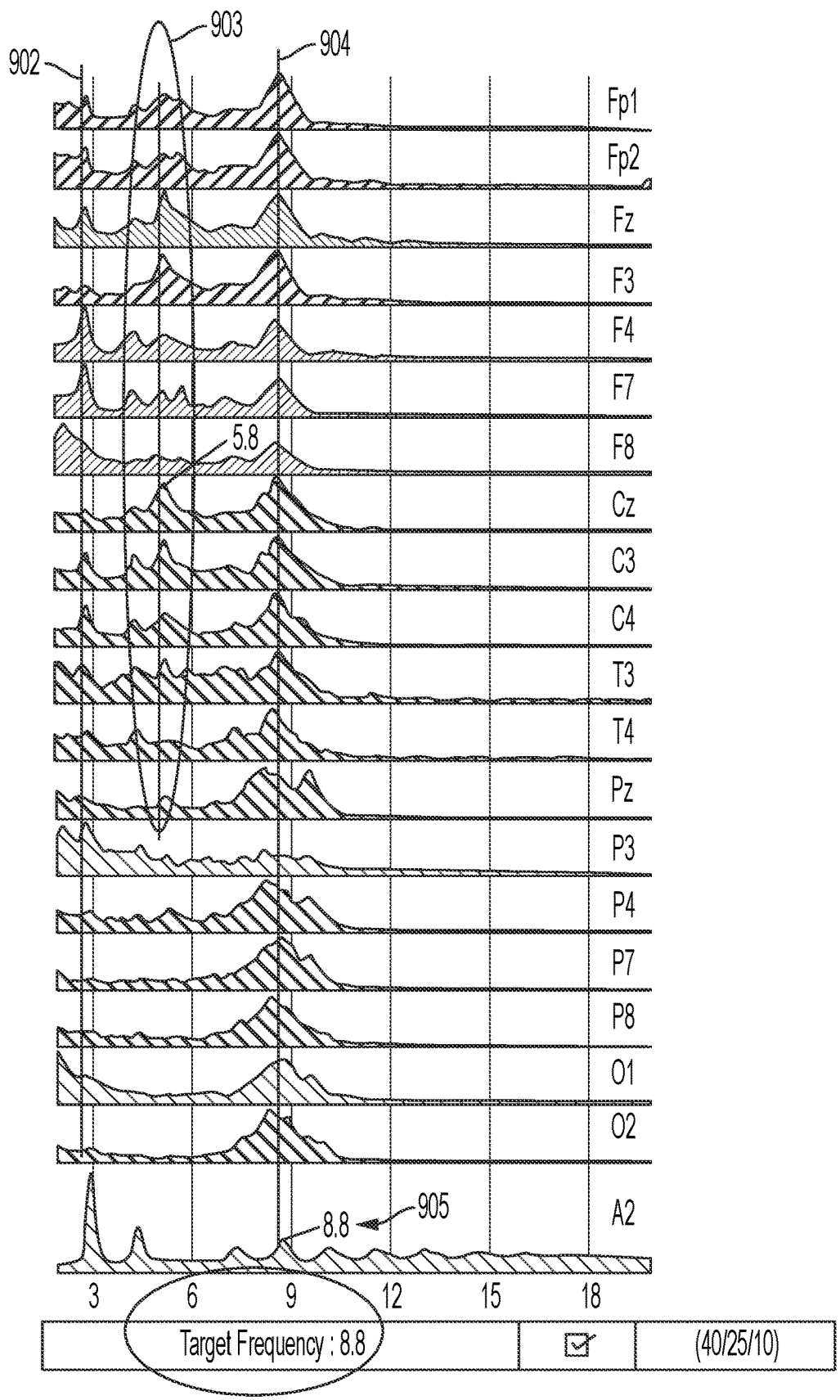
FIGS. 9A and 9B illustrate example qEEG Reports produced from EEG measurements taken from example subjects, and determination of homeostatic and target frequencies from the qEEG Reports.
Figure 9B:
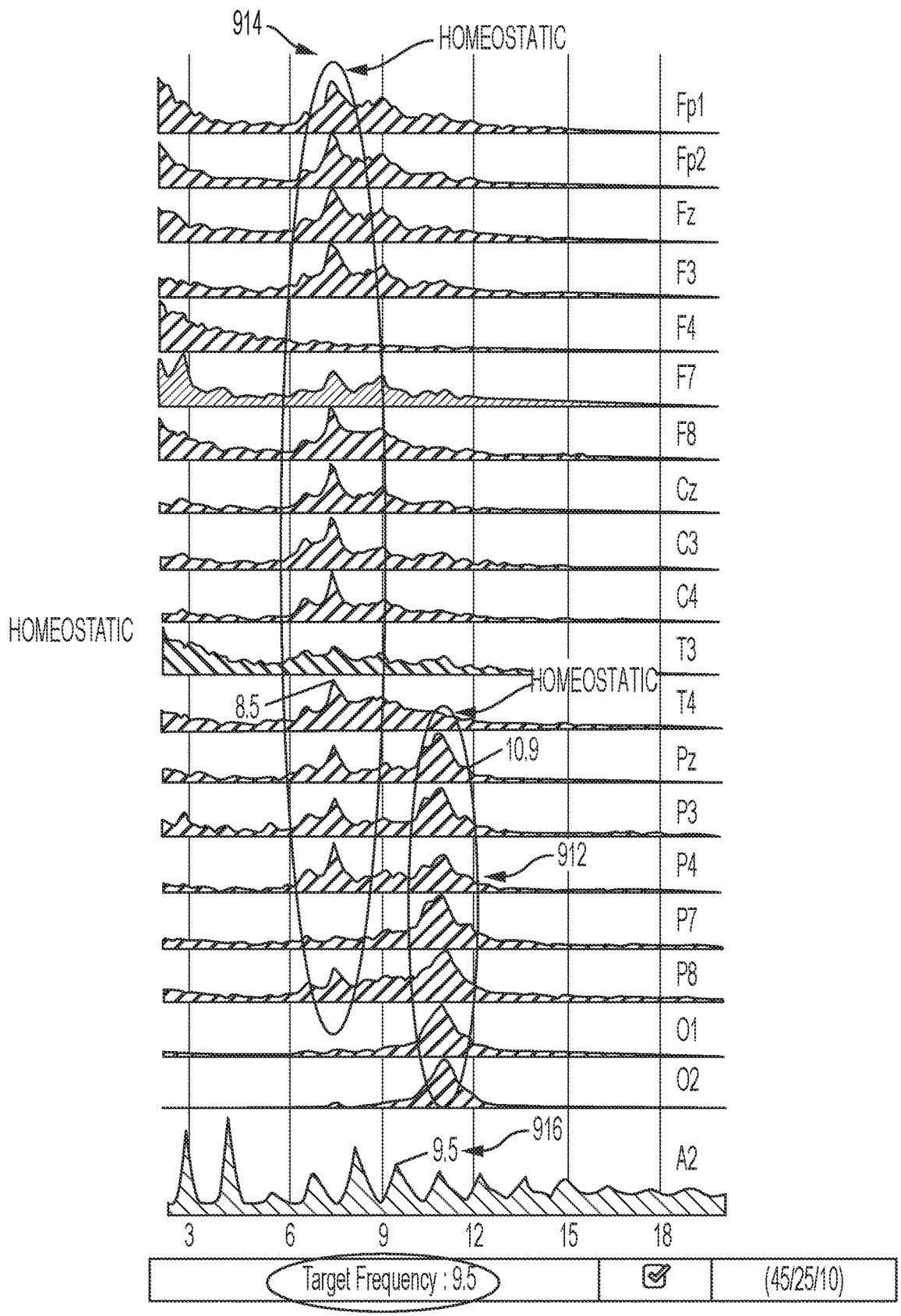

Referring now to FIGS. 9A and 9B, example qEEG Reports of two subjects are illustrated. As shown in FIGS. 9A and 9B, the EEG measurements across the 19 channels are analyzed with the heart rate (the A2 channel). The system may identify one or more homeostatic frequencies from the report as the frequency where the peaks (or spikes) in a threshold of channels number (e.g., 9, 10, 11, 12, 13, 14, 15, 16, 17, 18, 19, etc.) align (or approximately). The Target Frequency is then determined by identifying the frequency a which majority of the peaks of the 19 channels are approximately aligned between about 8-12 Hz, and that is close to and/or aligns with a heart rate peak. If the majority of the peaks align at more than one location aligned between about 8-12 Hz, the Target Frequency may be determined by, for example, taking an average of the frequencies at such locations, identifying a heart rate peak between such locations (and/or that is closest to one such location), identifying a heart rate peak that lies between such location and is closest to the average of the frequencies at such locations, or the like.

For example, in FIG. 9A, two Homeostatic Frequencies 903 (about 5.8 Hz) and 904 (about 8.8 Hz) are observed. Multiple Homeostatic Frequencies may be observer when, for example, certain neurons freeze at certain locations of the brain (e.g., because of trauma or one or more of the disorders discussed above, substance abuse, or the like. In FIG. 9A, the Target Frequency is also the Homeostatic Frequency 904 (about 8.8 Hz) because it is the only Homeostatic Frequency that lies between 8-12 Hz, and all of the channels (as well as the heart rate) have a peak around that frequency. As such the treatment protocols are determined to move the Homeostatic frequency 903 (and/or the Greatest Frequency of each channel) towards the Target Frequency 904. Optionally, a heart rate artifact (902) may be observed and discarded if the peak frequencies for all or substantially all of the channels are aligned with a heart rate peak. Such heart rate artifacts may be indicative of a strong heartrate that appears to be overtaking the EEG.

Similarly, in FIG. 9B two homeostatic frequencies 914 (about 8.5 Hz) and 916 (about 10.9) are observed which are between 8-12 Hz. As such, the Target Frequency is determined as the heart rate peak 916 (e.g., about 9.5 Hz) that lies between 914 and 916.

The treatment plan as performed by the process block 104 attempts to bolster the subject's Homeostatic Frequency across some or all of the channels (to achieve a Target Frequency) by addressing three to five regions (zones) in the brain: the CZ (central zone), the FZ (frontal zone), the F3 (dorsal lateral prefrontal cortex) zones, F4 (right dorsal lateral prefrontal cortex) zone, and FPZ (Frontal Parietal Zone), which may be performed in this order of treatment. It should be noted that these areas of the brain have not previously been used in typical TMS treatments, since it was believed that stimulating the CZ zone would induce seizures. However, treatments in accordance with the embodiments of this disclosure allow for stimulation of these zones without seizure induction. Treating these locations in accordance with embodiments described herein substantiates growth of the Alpha brainwaves from the most primitive to the most advanced (i.e., back to front of the brain, respectively). Progressively, this decreases the amplitude of sedative and/or activating wavelengths outside the Homeostatic Frequency range while increasing the individualized amplitude within the Homeostatic Frequency range; this maximizes the subject's brain potential to improve and maintain rational thought and decrease many symptoms of depression, anxiety, alcohol/substance cravings, and improve sleep.

In accordance with embodiments of the present disclosure, the normal amplitude of the magnet power setting for the treatments under the standard protocols may be:

CZ Zone=5% to 25%
FZ Zone=5% to 25%
F3 Zone=5% to 25%
FPZ Zone=5% to 25% iTMS has three standard protocols: First set of 10 treatments (Standard Protocol 1); second set of 10 treatments (Standard Protocol 2); and third set of 10 treatments (Standard Protocol 3). It should be noted that while the disclosure describes use of 10 treatments, it is not so limiting, and any number of treatments from about 4-20 treatments may be performed for each of the protocols depending on the treatment plan generated for a subject and/or the progress of the subject during a treatments (as determined using qEEG measurements)

For example, a first standard iTMS protocol may be composed of performing a selected number (e.g., ten) iTMS treatments that initiate with about 40 total Trains across the CZ zone, the FZ zone, the F3 zone, and the FPZ zone, each of which is about 5-30 seconds, about 7-27 seconds, about 10-25 second, about 12-23 seconds, about 15-20 seconds, about 10 second, about 15 seconds, or the like, long and with a frequency as determined from the Target Frequency (e.g., the Target Frequency+/−1 Hz). Between each of the Trains there is a break of about, 5-50 seconds, about 10-45 seconds, about 15-40 seconds, about 20-35 seconds, about 25-30 seconds, about 30 seconds, about 25 seconds, about 35 seconds, or the like, where no magnetic impulses are introduced (i.e., the InterTrain interval). The number of total Trains may not be limiting, and may be about 30-70, about 35-65, about 40-60, about 45-55, about 30, about 40, about 50, about 60, or the like.

In accordance with embodiments of the present disclosure, the CZ zone is treated with about 5-30 Trains, about, 10-25 Trains, about 15-20 Trains, about 15 Trains, about 20 Trains, about 10 Trains, or the like, the FZ zone is treated with about, –30 Trains, about, 10-25 Trains, about 15-20 Trains, about 15 Trains, about 20 Trains, about 10 Trains, or the like, the F3 zone is treated with about –30 Trains, about, 10-25 Trains, about 15-20 Trains, about 15 Trains, about 20 Trains, about 10 Trains, or the like, and the FPZ zone is treated with about –30 Trains, about, 10-25 Trains, about 15-20 Trains, about 15 Trains, about 20 Trains, about 10 Trains, or the like; each with suitable InterTrain intervals. Each treatment may be performed once daily but there are cases where two treatments may occur with a three-hour break between treatments.

After the first set of treatments (e.g., 10), another qEEG may be performed (process block 105), which may be accompanied with traditional psychometric testing. In the process block 106, the qEEG Reports are compared to identify progress such as described herein with respect to FIGS. 3A-5. In the process block 107, the process blocks 104-106 may be repeated any desired number of times to achieve a desired result (e.g., produce a uniform single Homeostatic Frequency in all measured zones of the brain that is closer to and/or approximately aligns with the Target Frequency compared to the EEGs measurements from before the treatment (e.g., one or more, or even all, of the channels), maximize amplitudes of these frequencies, and decrease variability outside of the 8 Hz-12 Hz range). In accordance with embodiments of the present disclosure, each subsequent set of standard protocols may be performed in the same manner as the previous protocol except that the InterTrain is decreased for each of the CZ, FZ, F3 zones, and FPZ (e.g., in about 1-30 second increments, such as in ten second increments, in 5 second increments, or the like).

Note that after performing a treatment in accordance with a process block 104, the Target Frequency may adjust to a higher or lower hertz within the 8 Hz-12 Hz range. For example, as discussed above with respect to FIGS. 9A and 9B, updated Target Frequency may be determined based on new EEG measurements collected post the treatment. Specifically, a goal is to produce a uniformed Homeostatic Frequency in all measured zones of the brain, maximize amplitude of said frequencies, and decrease variability outside of the 8 Hz-12 Hz range. However, alignment of the heart (channel A2) with the transcending zones of the brain prove fruitful in context to overall balance and uniformity of the brain. At times, the subject may appear unbalanced as the heart rate does not align with all other zones of the brain per EEG. In this case, the average between the discrepancies act as the new Target Frequency for the subsequent 10 iTMS treatments.

Based on psychometric assessments, qEEGs, and PSD reports, embodiments of the present disclosure may adapt to different treatment locations and may require adjustment from the standard protocol, especially if the cortical zones of the summary graph remain subdued with little amplitude. This is largely related to underlining depression, anxiety, or similar disorders. In these cases, the protocol may start starts with about 100-1000 pulses, about 200-900 pulses, about 300-800 pulses, about 400-700 pulses, about 500-600 pulses, or the like on the magnet at about 5-50% amplitude (at F3); essentially this would change the protocol to one train per second for about 100-1000 pulses for about 10-20 treatments. Then another EEG and psychometric assessments take place to evaluate any deviations and growth of the cortical zone or improvements of depressive and/or anxiety symptoms. This new treatment protocol continues for two rounds of 10 treatments which may include adjustment in the frequency depending on the EEG and alignment of all leads with the heart rate (A2 lead). On this protocol, only one treatment occurs over 24 hours.

If this does not lead to a reduction in psychometric scores or increased movement in summary graph results, the F3 zone is changed to the F4 zone of the brain for stimulation implementing the same protocol as discussed above with respect to F3. Again, only one treatment occurs within 24 hours when implementing this protocol. Another qEEG summary graph and psychometric screening panel is complete after 10 treatments; research has shown there are only two rounds of 10 treatments with this protocol. This is because balance in zones of the brain is being obtained with the protocol.

Providers may, optionally, add an additional protocol treating FpZ after considering the Anxiety Psychometric score Additionally, this tends to work well with patients who experience poor impulse control, hyperactivity, decreased concentration, irritability and chronic substance dependence. As described above, the addition of FPZ in at about 5-50-trains with about 5-25% amplitude of the strength of the magnet for 10 treatments is utilized. After the first set of treatments (e.g., 10), another qEEG may be performed (process block 105), which may be accompanied with traditional psychometric testing.

Embodiments of the present disclosure are applicable to the diagnosis and treatment of all neurological or mental disease states, including, but not limited to, Major Depressive Disorder ("MDD"), addictions of various types, anxiety, sleep disorders, substance abuse, traumatic brain injury/concussion, Attention Deficit Hyperactivity Disorder ("ADHD"), issues associated with menopause, executive functions, early onset Dementia, eating disorders, tinnitus, anger problems, short-term memory loss, Obsessive-Compulsive Disorder ("OCD"), migraines, improvement of athletic performance, balance problems, pain disorders, and other brain disorders.

In accordance with embodiments of the present disclosure, and as also described herein, processes performed within the data processing system 110 are configured to perform certain aspects as described with respect to the process blocks of FIG. 1 and produce outputs as described with respect to FIGS. 3A-5. As will be appreciated by one skilled in the art, aspects of the present disclosure may be embodied as a system, method, process, and/or program product. Accordingly, aspects of the present disclosure may take the form of an entirely hardware embodiment, an entirely software embodiment (including firmware, resident software, micro-code, etc.), or embodiments combining software and hardware aspects that may all generally be referred to herein as a "circuit," "circuitry," or "system." Furthermore, aspects of the present disclosure may take the form of a program product embodied in one or more computer-readable storage medium(s) having computer readable program code embodied thereon. (However, any combination of one or more computer-readable medium(s)

may be utilized. The computer-readable medium may be a computer-readable signal medium or a computer-readable storage medium.)

A computer-readable storage medium may be, for example, but not limited to, an electronic, magnetic, optical, electromagnetic, infrared, biologic, atomic, or semiconductor system, apparatus, controller, or device, or any suitable combination of the foregoing. More specific examples (a non-exhaustive list) of the computer-readable storage medium may include the following: an electrical connection having one or more wires, a portable computer diskette, a hard disk, a random access memory ("RAM"), a read-only memory ("ROM"), an erasable programmable read-only memory ("EPROM" or Flash memory), an optical fiber, a portable compact disc read-only memory ("CD-ROM"), an optical storage device, a magnetic storage device, or any suitable combination of the foregoing. In the context of this document, a computer-readable storage medium may be any tangible medium that can contain or store a program for use by or in connection with an instruction execution system, apparatus, controller, or device. Program code embodied on a computer readable signal medium may be transmitted using any appropriate medium, including but not limited to wireless, wire line, optical fiber cable, RF, etc., or any suitable combination of the foregoing.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, controller, or device.

The flowchart diagram and block diagrams in the figures illustrate architecture, functionality, and operation of possible implementations of systems, methods, processes, and program products according to various embodiments of the present disclosure. In this regard, each block in the flowchart diagram or block diagrams may represent a module, segment, or portion of code, which includes one or more executable program instructions for implementing the specified logical functions. It should also be noted that, in some implementations, the functions noted in the blocks may occur out of the order noted in the figures. For example, two blocks shown in succession may, in fact, be executed substantially concurrently, or the blocks may sometimes be executed in the reverse order, depending upon the functionality involved.

Modules implemented in software for execution by various types of processors may, for instance, include one or more physical or logical blocks of computer instructions which may, for instance, be organized as an object, procedure, or function. Nevertheless, the executables of an identified module need not be physically located together, but may include disparate instructions stored in different locations which, when joined logically together, include the module and achieve the stated purpose for the module. Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The data may provide electronic signals on a system or network.

These program instructions may be provided to a processor and/or controller of a general-purpose computer, special purpose computer, or other programmable data processing apparatus (e.g., controller) to produce a machine, such that the instructions, which execute via the processor of the computer or other programmable data processing apparatus, create means for implementing the functions/acts specified in the flowchart and/or block diagram block or blocks.

It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. For example, a module may be implemented as a hardware circuit comprising custom VLSI circuits or gate arrays, off-the-shelf semiconductors such as logic chips, transistors, controllers, or other discrete components. A module may also be implemented in programmable hardware devices such as field programmable gate arrays, programmable array logic, programmable logic devices, or the like.

Computer program code, i.e., instructions, for carrying out operations for embodiments of the present disclosure may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider).

These program instructions may also be stored in a computer-readable storage medium that can direct a computer, other programmable data processing apparatus, controller, or other devices to function in a particular manner, such that the instructions stored in the computer-readable medium produce an article of manufacture including instructions which implement the function/act specified in the flowchart and/or block diagram block or blocks.

The program instructions may also be loaded onto a computer, other programmable data processing apparatus, controller, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

One or more databases may be included in a host for storing and providing access to data for the various implementations. One skilled in the art will also appreciate that, for security reasons, any databases, systems, or components of the present disclosure may include any combination of databases or components at a single location or at multiple locations, wherein each database or system may include any of various suitable security features, such as firewalls, access codes, encryption, de-encryption and the like. The database may be any type of database, such as relational, hierarchical, object-oriented, and/or the like. Common database products that may be used to implement the databases include DB2 by IBM, any of the database products available from Oracle Corporation, Microsoft Access by Microsoft Corporation, or any other database product. The database may be organized in any suitable manner, including as data tables or lookup tables.

Association of certain data may be accomplished through any data association technique known and practiced in the art. For example, the association may be accomplished either manually or automatically. Automatic association techniques may include, for example, a database search, a database merge, GREP, AGREP, SQL, and/or the like. The association step may be accomplished by a database merge function, for example, using a key field in each of the manufacturer and retailer data tables. A key field partitions the database according to the high-level class of objects defined by the key field.

For example, a certain class may be designated as a key field in both the first data table and the second data table, and the two data tables may then be merged on the basis of the class data in the key field. In these embodiments, the data corresponding to the key field in each of the merged data tables is preferably the same. However, data tables having similar, though not identical, data in the key fields may also be merged by using AGREP, for example.

Reference may be made herein to "configuring" a device. It should be understood that this may include selecting predefined logic blocks and logically associating them, such that they provide particular logic functions, which includes monitoring or control functions. It may also include programming computer software-based logic of retrofit control device, wiring discrete hardware components, or a combination of any or all of the foregoing.

Reference throughout this specification to "one embodiment," "embodiments," or similar language means that a particular feature, structure, or characteristic described in connection with the embodiments is included in at least one embodiment of the present disclosure. Thus, appearances of the phrases "in one embodiment," "in an embodiment," "embodiments," and similar language throughout this specification may, but do not necessarily, all refer to the same embodiment. Furthermore, the described features, structures, aspects, and/or characteristics of the disclosure may be combined in any suitable manner in one or more embodiments. Correspondingly, even if features may be initially claimed as acting in certain combinations, one or more features from a claimed combination can in some cases be excised from the combination, and the claimed combination can be directed to a sub-combination or variation of a sub-combination.

In the descriptions herein, numerous specific details are provided, such as examples of programming, software modules, user selections, network transactions, database queries, database structures, hardware modules, hardware circuits, hardware chips, controllers, etc., to provide a thorough understanding of embodiments of the disclosure. One skilled in the relevant art will recognize, however, that the disclosure may be practiced without one or more of the specific details, or with other methods, components, materials, and so forth. In other instances, well-known structures, materials, or operations may be not shown or described in detail to avoid obscuring aspects of the disclosure.

Figure 8:
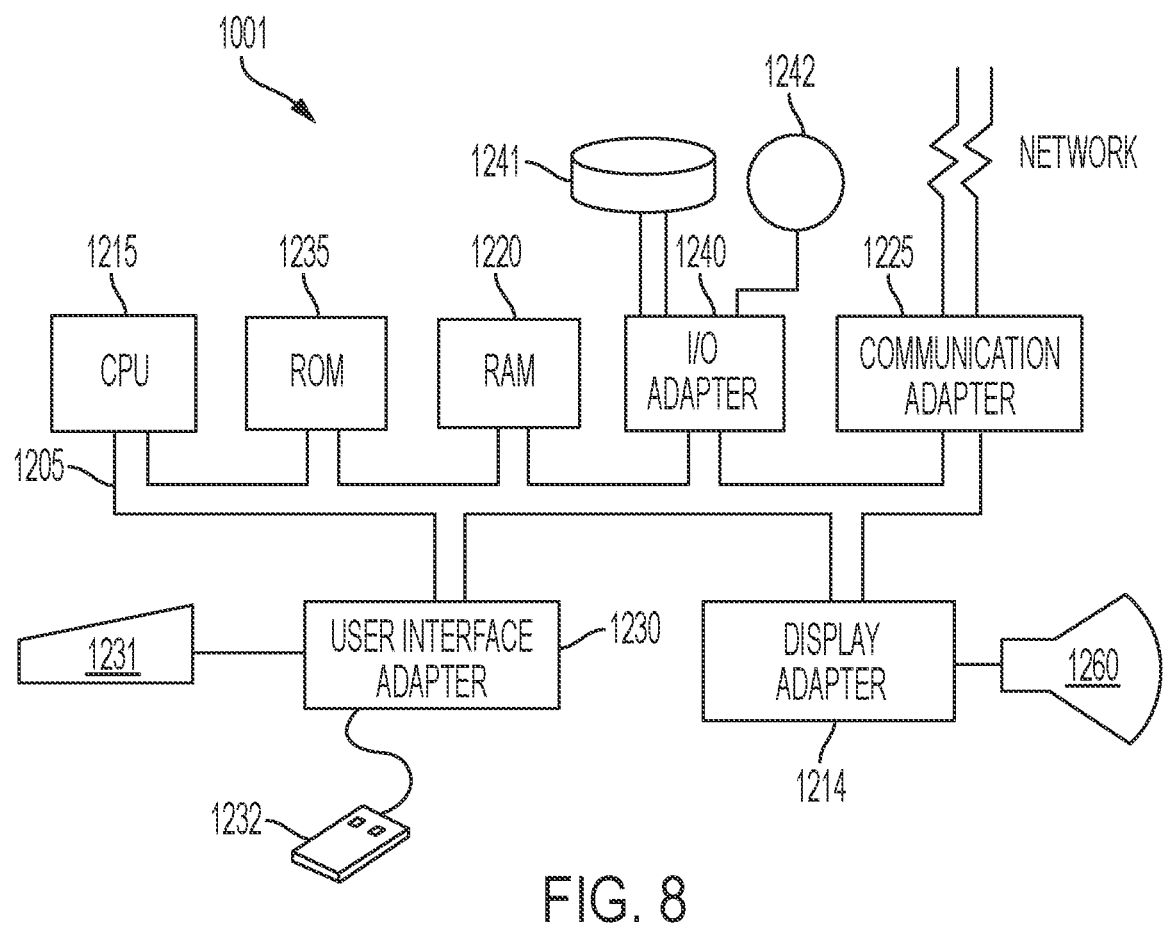
FIG. 8 illustrates a block diagram of a data processing system configured in accordance with embodiments of the present disclosure.

With reference now to FIG. 8, a block diagram illustrating a data processing system is depicted in which aspects of embodiments of the disclosure may be implemented. Data processing system 1001 may employ a peripheral component interconnect ("PCI") local bus architecture. Although the depicted example employs a PCI bus, other bus architectures such as Accelerated Graphics Port ("AGP") and Industry Standard Architecture ("ISA") may be used, among others. Processor 1215, volatile memory 1220, and non-volatile memory 1235 may be connected to the local bus 1205 through a PCI Bridge (not shown). The PCI Bridge also may include an integrated memory controller and cache memory for processor 1215. Additional connections to the local bus 1205 may be made through direct component interconnection or through add-in boards. In the depicted example, a LAN adapter 1225, small data processing system interface ("SCSI") host bus adapter (not shown), and expansion bus interface (not shown) may be connected to the local bus 1205 by direct component connection. In contrast, an audio adapter (not shown), a graphics adapter (not shown), and a display adapter 1214 and display 1260 may be coupled to the local bus 1205 by add-in boards inserted into expansion slots. A user interface adapter 1230 may provide a connection for a keyboard 1231 and a mouse 1232.

An I/O adapter 1240 may provide a connection for a hard disk drive 1241, a tape drive, and a CD-ROM/DVD drive 1242.

An operating system may be run on processor 1215 and used to coordinate and provide control of various components within the data processing system 1001. The operating system may be a commercially available operating system. An object-oriented programming system such as Java may run in conjunction with the operating system and provide calls to the operating system from Java programs or programs executing on the system 1001. Instructions for the operating system, the object-oriented operating system, and programs may be located on the non-volatile memory 1235 storage devices, such as the hard disk drive 1241, and may be loaded into the volatile memory 1220 for execution by the processor 1215.

Those of ordinary skill in the art will appreciate that the hardware in FIG. 8 may vary depending on the implementation. Other internal hardware or peripheral devices, such as flash ROM (or equivalent nonvolatile memory) or optical disk drives and the like, may be used in addition to or in place of the hardware depicted in FIG. 8. Also, the processes of the present disclosure may be applied to a multiprocessor data processing system.

As another example, the data processing system 1001 may be a stand-alone system configured to be bootable without relying on some type of network communication interface, whether or not the data processing system 1001 includes some type of network communication interface. As a further example, the data processing system 1001 may be an embedded controller, which is configured with ROM and/or flash ROM providing nonvolatile memory storing operating system files or user-generated data.

The depicted example in FIG. 8 and above-described examples are not meant to imply architectural limitations. Further, a computer program form of the present disclosure may reside on any computer-readable storage medium (i.e., floppy disk, compact disk, hard disk, tape, ROM, RAM, etc.) used by a data processing system. (The terms "computer," "system," and "data processing system" are used interchangeably herein.)

Reference may be made herein to a device, circuit, circuitry, system, or module "configured to" perform a particular function or functions. It should be understood that this may include selecting predefined logic blocks and logically associating them, such that they provide particular logic functions, which includes monitoring or control functions. It may also include programming computer software-based logic, wiring discrete hardware components, or a combination of any or all of the foregoing.

Reference throughout this specification to "an embodiment," "embodiments," "certain embodiments," "various embodiments," or similar language means that a particular feature, structure, or characteristic described in connection with the embodiments is included in at least one embodiment of the present disclosure. Thus, appearances of the phrases "in embodiments," "in an embodiment," "embodiments," "in certain embodiments," and similar language throughout this specification may, but do not necessarily, all refer to the same embodiment. Furthermore, the described features, structures, aspects, or characteristics of the disclosure may be combined in any suitable manner in one or more embodiments. Correspondingly, even if features may be initially claimed as acting in certain combinations, one or more features from a claimed combination can in some cases be excised from the combination, and the claimed combination can be directed to a sub-combination or variation of a sub-combination.

The terminology used herein is for the purpose of describing particular embodiments and applications only and is not intended to be limiting of the disclosure. In the descriptions herein, numerous specific details are provided, such as examples of activities, circumstances, services, faults, errors, responses, reactions, processor activities, operations, events, mechanisms, software threads, cyberattacks, signals, or actions, programming, software modules, designer, manufacturer, or end user selections, network transactions, database queries, database structures, hardware modules, hardware circuits, hardware chips, controllers, etc., to provide a thorough understanding of embodiments of the disclosure. One skilled in the relevant art will recognize, however, that the disclosure may be practiced without one or more of the specific details, or with other methods, components, materials, activities, circumstances, services, faults, errors, responses, reactions, processor activities, operations, events, mechanisms, software threads, cyberattacks, signals, and so forth. In other instances, well-known structures, materials, or operations may be not shown or described in detail to avoid obscuring aspects of the disclosure.

Benefits, advantages, and solutions to problems may have been described herein with regard to specific embodiments or applications. However, the benefits, advantages, solutions to problems, and any element(s) that may cause any benefit, advantage, or solution to occur or become more pronounced are not to be construed as critical, required, or essential features or elements of any or all the claims. Those skilled in the art having read this disclosure will recognize that changes and modifications may be made to the embodiments without departing from the scope of the present disclosure. It should be appreciated that the particular implementations and applications shown and described herein may be illustrative of the disclosure and are not intended to otherwise limit the scope of the present disclosure in any way. Other variations may be within the scope of the following claims. Headings herein are not intended to limit the disclosure, embodiments of the disclosure, or other matter disclosed under the headings.

Herein, the term "or" may be intended to be inclusive, wherein "A or B" includes A or B and also includes both A and B. As used herein, the term "or" when used in the context of a listing of entities, refers to the entities being present singly or in combination. Thus, for example, the phrase "A, B, C, or D" includes A, B, C, and D individually, but also includes any and all combinations and sub-combinations of A, B, C, and D. As used herein, the term "and/or" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D. As used herein, the singular forms "a," "an," and "the" may be intended to include the plural forms as well, unless the context clearly indicates otherwise.

The corresponding structures, materials, acts, and equivalents of all means or step plus function elements in the claims may be intended to include any structure, material, or act for performing the function in combination with other claimed elements as specifically claimed.

What is claimed is:

1. A method for treatment of a mental disorder of a subject, the method comprising, by a processor:
   receiving a first set of electroencephalography ("EEG") measurements, the first set of EEG measurements corresponding to brain activity at one or more of a plurality of zones of a brain of the subject;
   determining, based on the first set of EEG measurements, a target frequency for the subject, the target frequency being an EEG frequency where the brain of the subject operates optimally across a plurality of EEG channels in an alpha brainwave, wherein determining the target frequency comprises:
      identifying, across the plurality of EEG channels, a first homeostatic frequency as a frequency that lies within a threshold distance of a first set of maximum power spectral density (PSD) values of a majority of the plurality of EEG channels,
      identifying a heart rate peak frequency that is closest to the first homeostatic frequency, and
      assigning the heart rate peak frequency as the target frequency;
   generating, based on the target frequency, a treatment protocol for the subject, the treatment protocol comprising one or more individualized transcranial magnetic stimulation (TMS) treatments that each include application of a plurality of magnetic stimulation pulses for a defined time period and at a frequency of about the target frequency; and
   causing a TMS system to provide the one or more individualized TMS treatments to the subject in accordance with the treatment protocol.

2. The method as recited in claim 1, wherein the one or more individualized TMS treatments each comprise application of the plurality of magnetic stimulation pulses to a Cz zone, a Fz zone, an F3 zone, and an FPZ zone of the brain of the subject, wherein the Cz, Fz, F3, and FPZ zones correspond to zones designated within a 10-20 system of electrode placement.

3. The method as recited in claim 1, wherein determining the target frequency further comprises:
   identifying, across the plurality of EEG channels, a second homeostatic frequency as a second frequency that lies within a second threshold distance of a second set of PSD values of a majority of the plurality of EEG channels;
   identifying the heart rate frequency as being at least one of the following: a second heart rate frequency that lies between the first homeostatic frequency and the second homeostatic frequency, a second heart rate frequency that is closest to an average of the first homeostatic frequency and the second homeostatic frequency, or a second heart rate frequency that is closest to one of the first homeostatic frequency and the second homeostatic frequency.

4. The method as recited in claim 1, wherein a treatment interval is interspersed between two consecutive TMS treatments.

5. The method as recited in claim 1, further comprising:
receiving, after the causing the TMS system to provide the one or more treatments to the subject in accordance with the treatment protocol, a second set of EEG measurements;
updating, based on the second set of EEG measurements, the target frequency to generate an updated target frequency; and
generating based on the updated target frequency, a second treatment protocol.

6. The method as recited in claim 5, wherein an intertrain interval of the treatment protocol is different than an intertrain interval of the second treatment protocol.

7. The method as recited in claim 1, wherein the target frequency is about 8-12 Hz.

8. The method as recited in claim 1, wherein the target frequency is updated to align with the heart rate frequency of the subject.

9. The method as recited in claim 1, further comprising:
receiving, after the causing the TMS system to provide the one or more treatments to the subject in accordance with the treatment protocol, a second set of EEG measurements; and
displaying an improvement in the mental disorder in response to identifying reductions in differences between maximum PSD values associated with one or more of the plurality of EEG channels, as determined based on the second set of EEG measurements, and the target frequency.

10. The method as recited in claim 9, further comprising:
determining, based on a comparison of the first set of EEG measurements and the second set of EEG measurements, a change in the mental disorder that is less than a threshold; and
updating the treatment protocol to include a first TMS treatment that comprises application of about 200 to 400 magnetic stimulation pulses at about 30% amplitude to the F3 zone of the brain of the subject.

11. The method as recited in claim 1, wherein the mental disorder comprises at least one of the following: traumatic brain injury; tinnitus; short term memory issues; substance abuse disorder; sleep disorder; anxiety; depression; post-traumatic stress disorder; attention deficit hyperactivity disorder; bi-polar disorder; dementia; sleep disorders; balance and fine motor skills disorder; reading comprehension; verbal communication, and working memory disorders; night vision disorders; or colors and shape vision disorders.

12. A system for treatment of a mental disorder of a subject, the system comprising:
a processor; and
a non-transitory computer-readable medium comprising programming instructions that when executed by the processor will cause the processor to:
receive a first set of electroencephalography ("EEG") measurements, the first set of EEG measurements corresponding to brain activity at one or more of a plurality of zones of a brain of the subject;
determine, based on the first set of EEG measurements, a target frequency for the subject, the target frequency being an EEG frequency where the brain of the subject operates optimally across a plurality of EEG channels in an alpha brainwave, wherein determining the target frequency comprises:
identifying, across the plurality of EEG channels, a first homeostatic frequency as a frequency that lies within a threshold distance of a first set of maximum power spectral density (PSD) values of a majority of the plurality of EEG channels,
identifying a heart rate peak frequency that is closest to the first homeostatic frequency, and
assigning the heart rate peak frequency as the target frequency;
generate, based on the target frequency, a treatment protocol for the subject, the treatment protocol comprising one or more individualized transcranial magnetic stimulation (TMS) treatments that each include application of a plurality of magnetic stimulation pulses for a defined time period and at a frequency of about the target frequency; and
cause a TMS system to provide the one or more individualized TMS treatments to the subject in accordance with the treatment protocol.

13. The system as recited in claim 12, wherein the one or more individualized TMS treatments each comprise application of the plurality of magnetic stimulation pulses to a Cz zone, a Fz zone, an F3 zone, and an FPZ zone of the brain of the subject, wherein the Cz, Fz, F3, and FPZ zones correspond to zones designated within a 10-20 system of electrode placement.

14. The system as recited in claim 12, wherein the programming instructions that cause the processor to determine the target frequency comprise programming instructions to cause the processor to:
identify, across the plurality of EEG channels, a second homeostatic frequency as a second frequency that lies within a second threshold distance of a second set of PSD values of a majority of the plurality of EEG channels;
identify the heart rate frequency as being at least one of the following: a second heart rate frequency that lies between the first homeostatic frequency and the second homeostatic frequency, a second heart rate frequency that is closest to an average of the first homeostatic frequency and the second homeostatic frequency, or a second heart rate frequency that is closest to one of the first homeostatic frequency and the second homeostatic frequency.

15. The system as recited in claim 12, wherein a treatment interval is interspersed between two consecutive TMS treatments.

16. The system as recited in claim 12, further comprising programming instructions that when executed by the processor will cause the processor to:
receive, after the causing the TMS system to provide the one or more treatments to the subject in accordance with the treatment protocol, a second set of EEG measurements;
update, based on the second set of EEG measurements, the target frequency to generate an updated target frequency; and
generate, based on the updated target frequency, a second treatment protocol.

17. The system as recited in claim 16, wherein an intertrain interval of the treatment protocol is different than an intertrain interval of the second treatment protocol.

18. The system as recited in claim 12, wherein the target frequency is about 8-12 Hz.

19. The system as recited in claim 12, wherein the target frequency is updated to align with the heart rate frequency of the subject.

20. The system as recited in claim 12, further comprising programming instructions that when executed by the processor will cause the processor to:
- receive, after the causing the TMS system to provide the one or more treatments to the subject in accordance with the treatment protocol, a second set of EEG measurements; and
- display an improvement an improvement in the mental disorder in response to identifying reductions in differences between maximum PSD values associated with one or more of the plurality of EEG channels, as determined based on the second set of EEG measurements, and the target frequency.

* * * * *